(12) United States Patent
Burdulis, Jr. et al.

(10) Patent No.: US 6,730,102 B1
(45) Date of Patent: May 4, 2004

(54) SYSTEMS, DEVICES AND METHODS FOR DEPLOYING NEEDLES

(75) Inventors: Albert Burdulis, Jr., San Francisco, CA (US); Joshua Stafford, Fremont, CA (US)

(73) Assignee: Abbott Laboratories, Abbott Park, IL (US)

(*) Notice: Subject to any disclaimer, the term of this patent is extended or adjusted under 35 U.S.C. 154(b) by 101 days.

(21) Appl. No.: 09/707,727

(22) Filed: Nov. 6, 2000

(51) Int. Cl.[7] .............................................. A61B 17/04
(52) U.S. Cl. ...................................... 606/144; 606/148
(58) Field of Search ........................ 600/170; 606/153, 606/154, 155, 139, 144, 151, 158; 112/80.73

(56) References Cited

U.S. PATENT DOCUMENTS

| 312,408 | A | 2/1885 | Wackerhagen |
| 659,422 | A | 10/1900 | Shidler |
| 2,127,903 | A | 8/1938 | Bowen |
| 2,397,823 | A | 4/1946 | Walter |

(List continued on next page.)

FOREIGN PATENT DOCUMENTS

| DE | 4210724 C1 | 7/1993 |
| DE | 9217932 | 7/1993 |
| EP | 140557 A2 | 5/1985 |
| EP | 207545 A1 | 1/1987 |

(List continued on next page.)

OTHER PUBLICATIONS

Elgin National Watch Company, Product Brochure entitled "Elgiloy®, A Cobalt Nickel Spring Alloy," 33 pages.
Faulkner, Catherine B., Letter regarding "VasoSeal Vascular Hemostasis," *Datascope*, New Jersey, 1 page only.
Laurus Medical Corporation, "Endoscopic Suturing Made Simple," The Laurs ND–2600 Needle Driver, Irvine, CA., 1 page.

(List continued on next page.)

*Primary Examiner*—Peter Nerbun
(74) *Attorney, Agent, or Firm*—Joseph A. Twarowski

(57) ABSTRACT

A needle deployment device is provided. The needle deployment device comprises a body, a plurality of medical needles displaceably mounted on the body and an actuator on the body. The actuator is actuatable in response to pressurizing a fluid so as to cause the needles to displace relative to the body. It has been found that the device can be used advantageously as a suture placement device for placing suture elements through walls of vessels, and the like, during, for example, coronary artery bypass graft (CABG)surgery, or the like. Furthermore, a medical system comprising at least two bodies, a plurality of needles displaceably mounted on each body and an actuator on each body is provided. Each actuator is selectively actuatable in response to pressurizing a fluid so as to cause the needles to be displaced relative to their associated bodies. A method of performing a medical procedure is also provided. The method comprises pressurizing a fluid, actuating an actuator of a needle deployment device in response to pressurizing the fluid and causing a plurality of needles to displace in response to actuating the actuator.

38 Claims, 25 Drawing Sheets

U.S. PATENT DOCUMENTS

| | | |
|---|---|---|
| 2,646,045 A | 7/1953 | Priestley |
| 2,959,172 A | 11/1960 | Held |
| 3,104,666 A | 9/1963 | Hale et al. |
| 3,470,875 A | 10/1969 | Johnson |
| 3,653,388 A | 4/1972 | Tenckhoff |
| 3,665,926 A | 5/1972 | Flores |
| 3,776,237 A | 12/1973 | Hill et al. |
| 3,820,544 A | 6/1974 | Semm |
| 3,926,194 A | 12/1975 | Greenberg et al. |
| 3,939,820 A | 2/1976 | Grayzel |
| 4,018,228 A | 4/1977 | Goosen |
| 4,109,658 A | 8/1978 | Hughes |
| 4,161,951 A | 7/1979 | Scanlan, Jr. |
| 4,168,073 A | 9/1979 | LaRue |
| 4,182,339 A | 1/1980 | Hardy, Jr. |
| 4,216,776 A | 8/1980 | Downie et al. |
| 4,235,177 A | 11/1980 | Arbuckle |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,493,323 A | 1/1985 | Albright et al. |
| 4,553,543 A | 11/1985 | Amarasinghe |
| 4,587,969 A | 5/1986 | Gillis |
| 4,596,559 A | 6/1986 | Fleischhacker |
| 4,629,450 A | 12/1986 | Suzuki et al. |
| 4,651,733 A | 3/1987 | Mobin-Uddin |
| 4,723,549 A | 2/1988 | Wholey et al. |
| 4,738,666 A | 4/1988 | Fuqua |
| 4,744,364 A | 5/1988 | Kensey |
| 4,803,984 A | 2/1989 | Narayanan et al. |
| 4,836,205 A | 6/1989 | Barrett |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,926,860 A | 5/1990 | Stice et al. |
| 4,929,246 A | 5/1990 | Sinofsky |
| 4,935,027 A | 6/1990 | Yoon |
| 4,957,498 A | 9/1990 | Caspari et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,047,039 A | 9/1991 | Avant et al. |
| 5,059,201 A | 10/1991 | Asnis |
| 5,061,274 A | 10/1991 | Kensey |
| 5,078,721 A | 1/1992 | McKeating |
| 5,080,664 A | 1/1992 | Jain |
| 5,100,419 A | 3/1992 | Ehlers |
| 5,100,432 A | 3/1992 | Matsutani |
| 5,109,780 A | 5/1992 | Slouf et al. |
| 5,129,913 A | 7/1992 | Ruppert |
| 5,143,003 A * | 9/1992 | Dedmon ................. 112/80.73 |
| 5,147,373 A | 9/1992 | Ferzli |
| 5,160,339 A | 11/1992 | Chen et al. |
| 5,171,251 A | 12/1992 | Bregen et al. |
| 5,192,294 A | 3/1993 | Blake, III |
| 5,192,302 A | 3/1993 | Kensey et al. |
| 5,219,358 A | 6/1993 | Bendel et al. |
| 5,222,974 A | 6/1993 | Kensey et al. |
| 5,234,443 A | 8/1993 | Phan et al. |
| 5,242,427 A | 9/1993 | Bilweis |
| 5,250,033 A | 10/1993 | Evans et al. |
| 5,250,053 A | 10/1993 | Snyder |
| 5,254,126 A | 10/1993 | Filipi et al. |
| 5,258,003 A | 11/1993 | Ciaglia et al. |
| 5,279,311 A | 1/1994 | Snyder |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,292,309 A | 3/1994 | Van Tassel et al. |
| 5,292,332 A | 3/1994 | Lee |
| 5,293,881 A | 3/1994 | Green et al. |
| 5,295,993 A | 3/1994 | Green |
| 5,300,085 A | 4/1994 | Yock |
| 5,304,184 A | 4/1994 | Hathaway et al. |
| 5,304,185 A | 4/1994 | Taylor |
| 5,306,254 A | 4/1994 | Nash et al. |
| 5,312,024 A | 5/1994 | Grant et al. |
| 5,320,632 A | 6/1994 | Heidmueller |
| 5,336,229 A | 8/1994 | Noda |
| 5,336,230 A | 8/1994 | Leichtling et al. |
| 5,336,231 A | 8/1994 | Adair |
| 5,342,369 A | 8/1994 | Harryman, II |
| 5,354,312 A | 10/1994 | Brinkerhoff et al. |
| 5,364,408 A | 11/1994 | Gordon |
| 5,368,601 A | 11/1994 | Sauer et al. |
| 5,374,275 A | 12/1994 | Bradley et al. |
| 5,376,096 A | 12/1994 | Foster |
| 5,383,896 A | 1/1995 | Gershony et al. |
| 5,387,221 A | 2/1995 | Bisgaard |
| 5,387,227 A | 2/1995 | Grice |
| 5,395,332 A | 3/1995 | Ressemann et al. |
| 5,395,349 A | 3/1995 | Quiachon et al. |
| 5,397,325 A | 3/1995 | Delia Badia et al. |
| 5,403,329 A | 4/1995 | Hinchcliffe |
| 5,403,338 A | 4/1995 | Milo |
| 5,411,481 A | 5/1995 | Allen et al. |
| 5,413,571 A | 5/1995 | Katsaros et al. |
| 5,417,699 A | 5/1995 | Klein et al. |
| 5,425,705 A | 6/1995 | Evard et al. |
| 5,431,666 A | 7/1995 | Sauer et al. |
| 5,433,700 A | 7/1995 | Peters |
| 5,452,733 A | 9/1995 | Sterman et al. |
| 5,454,822 A | 10/1995 | Schöb et al. |
| 5,454,834 A | 10/1995 | Boebel et al. |
| 5,458,574 A | 10/1995 | Machold et al. |
| 5,470,338 A | 11/1995 | Whitfield et al. |
| 5,476,469 A | 12/1995 | Hathaway et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,480,407 A | 1/1996 | Wan et al. |
| 5,486,190 A | 1/1996 | Green |
| 5,489,295 A | 2/1996 | Piplani et al. |
| 5,496,332 A | 3/1996 | Sierra et al. |
| 5,507,744 A | 4/1996 | Tay et al. |
| 5,507,755 A | 4/1996 | Gresl et al. |
| 5,507,757 A | 4/1996 | Sauer et al. |
| 5,507,758 A | 4/1996 | Thomason et al. |
| 5,509,902 A | 4/1996 | Raulerson |
| 5,520,665 A | 5/1996 | Fleetwood |
| 5,520,702 A | 5/1996 | Sauer et al. |
| 5,527,321 A | 6/1996 | Hinchliffe |
| 5,527,322 A | 6/1996 | Klein et al. |
| D372,310 S | 7/1996 | Harnett |
| 5,531,700 A | 7/1996 | Moore et al. |
| 5,540,701 A | 7/1996 | Sharkey et al. |
| 5,540,704 A | 7/1996 | Gordon et al. |
| 5,545,171 A | 8/1996 | Sharkey et al. |
| 5,545,178 A | 8/1996 | Kensey et al. |
| 5,545,180 A | 8/1996 | Le et al. |
| 5,549,618 A | 8/1996 | Fleenor et al. |
| 5,554,162 A | 9/1996 | DeLange |
| 5,562,686 A | 10/1996 | Sauer et al. |
| 5,562,688 A | 10/1996 | Riza |
| 5,562,728 A | 10/1996 | Lazarus et al. |

| | | | | | | |
|---|---|---|---|---|---|---|
| 5,569,271 A | 10/1996 | Hoel | | EP | 542126 A3 | 5/1993 |
| 5,573,540 A | 11/1996 | Yoon | | EP | 568098 A2 | 11/1993 |
| 5,591,179 A | 1/1997 | Edelstein | | EP | 589409 A1 | 3/1994 |
| 5,591,206 A | 1/1997 | Moufarrège | | EP | 624343 A2 | 11/1994 |
| 5,593,421 A | 1/1997 | Bauer | | EP | 669103 A1 | 8/1995 |
| 5,603,718 A | 2/1997 | Xu | | EP | 568098 B1 | 10/1997 |
| 5,611,794 A | 3/1997 | Sauer et al. | | EP | 669102 B1 | 10/1998 |
| 5,613,974 A | 3/1997 | Andreas et al. | | EP | 669101 B1 | 9/1999 |
| 5,613,975 A | 3/1997 | Christy | | FR | 1059544 | 7/1952 |
| 5,643,289 A | 7/1997 | Sauer et al. | | JP | 2119866 A | 5/1990 |
| 5,669,917 A | 9/1997 | Sauer et al. | | JP | 542161 A | 2/1993 |
| 5,700,273 A | 12/1997 | Buelna et al. | | SU | 993922 | 2/1983 |
| 5,713,910 A | 2/1998 | Gordon et al. | | SU | 1093329 | 5/1984 |
| 5,716,369 A | 2/1998 | Riza | | SU | 1174036 | 8/1985 |
| 5,720,757 A | 2/1998 | Hathaway et al. | | SU | 1544383 | 2/1990 |
| 5,728,151 A | 3/1998 | Garrison et al. | | SU | 1648400 | 5/1991 |
| 5,741,276 A | 4/1998 | Poloyko et al. | | SU | 820810 | 6/1997 |
| 5,741,280 A | 4/1998 | Fleenor | | WO | WO 94/05213 | 3/1994 |
| 5,759,188 A | 6/1998 | Yoon | | WO | WO 94/27503 | 12/1994 |
| 5,766,183 A | 6/1998 | Sauer | | WO | WO 94/28801 | 12/1994 |
| 5,766,186 A | 6/1998 | Faraz et al. | | WO | WO 95/05121 | 2/1995 |
| 5,779,719 A | 7/1998 | Klein et al. | | WO | WO 95/35065 | 2/1995 |
| 5,792,151 A | 8/1998 | Heck et al. | | WO | WO 95/35065 | 12/1995 |
| 5,799,661 A | 9/1998 | Boyd et al. | | WO | WO 97/03613 | 2/1997 |
| 5,810,850 A | 9/1998 | Hathaway et al. | | WO | WO 97/10764 | 3/1997 |
| 5,817,113 A | 10/1998 | Gifford, III et al. | | WO | WO 97/13461 | 4/1997 |
| 5,820,631 A | 10/1998 | Nobles | | WO | WO 97/17901 | 5/1997 |
| 5,824,010 A | 10/1998 | McDonald | | WO | WO 97/20505 | 6/1997 |
| 5,836,955 A | 11/1998 | Buelna et al. | | WO | WO 00/12013 | 3/2000 |
| 5,836,956 A | 11/1998 | Buelna et al. | | | | |
| 5,846,253 A | 12/1998 | Buelna et al. | | | | |
| 5,860,990 A | 1/1999 | Nobles et al. | | | | |
| 5,860,991 A | 1/1999 | Klein et al. | | | | |
| 5,902,311 A | 5/1999 | Andreas et al. | | | | |
| 5,904,697 A | 5/1999 | Gifford, III et al. | | | | |
| 5,951,590 A | 9/1999 | Goldfarb | | | | |
| 5,954,732 A | 9/1999 | Hart et al. | | | | |
| 6,036,699 A | 3/2000 | Andreas et al. | | | | |
| 6,048,351 A | 4/2000 | Gordon et al. | | | | |
| 6,117,144 A | 9/2000 | Nobles et al. | | | | |
| 6,120,520 A * | 9/2000 | Saadat et al. ............... 600/170 | | | | |

FOREIGN PATENT DOCUMENTS

| | | |
|---|---|---|
| EP | 047887 A1 | 3/1992 |
| EP | 478358 A1 | 4/1992 |

OTHER PUBLICATIONS

Product Brochure, Laurus Medical Corporation, Irvine, CA "The Laurus In–Line Endoscopic Suturing Device" (Oct. 1994) 1 page.

Rema–Medizintechnik GmbH, Product Brochure entitled "REMA," 7 pages.

Sutura™, "A New Choice In Vascular Suturing . . . ," Let Sutura Show You—TCT Booth 846, Fountain Valley, CA.; www.suturainc.com., 1 page only.

* cited by examiner

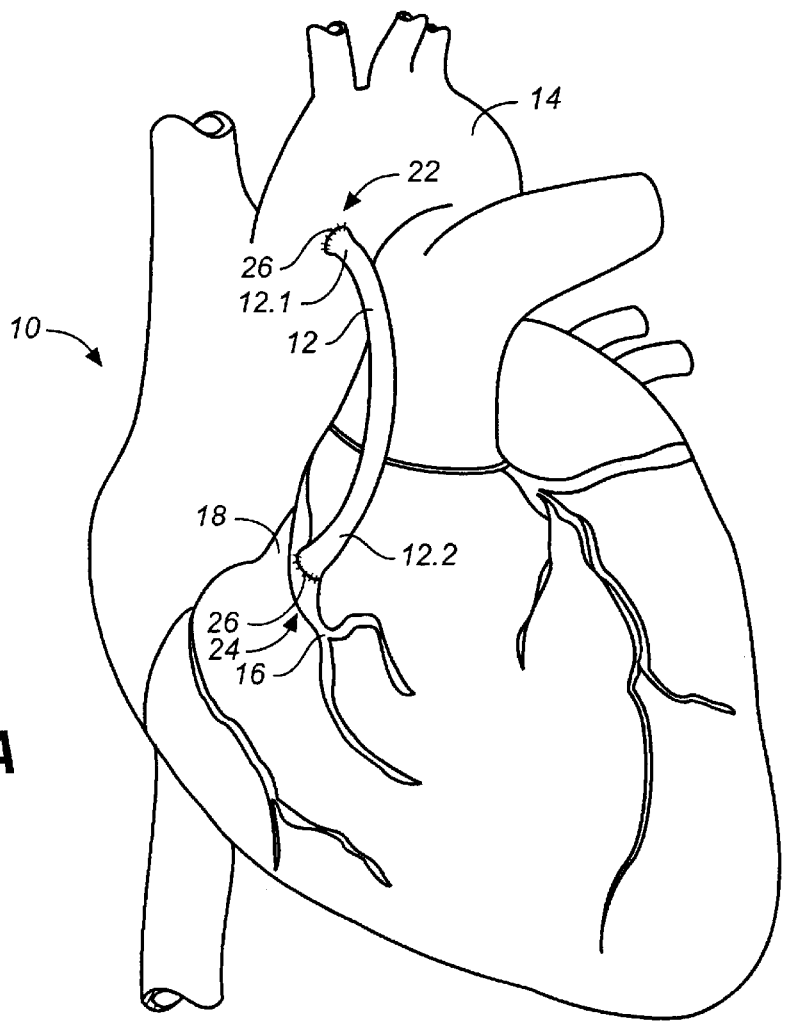
FIG._1A
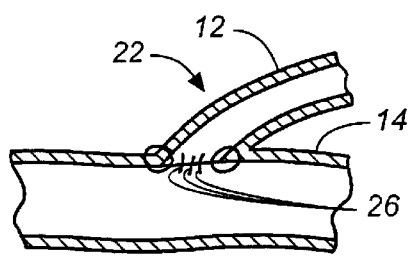
FIG._1B
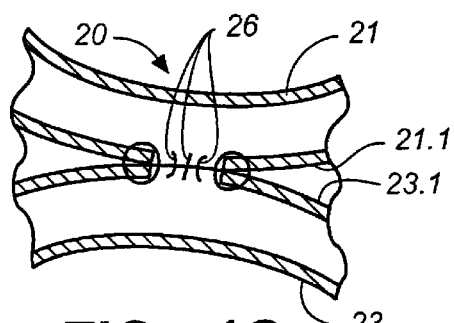
FIG._1C

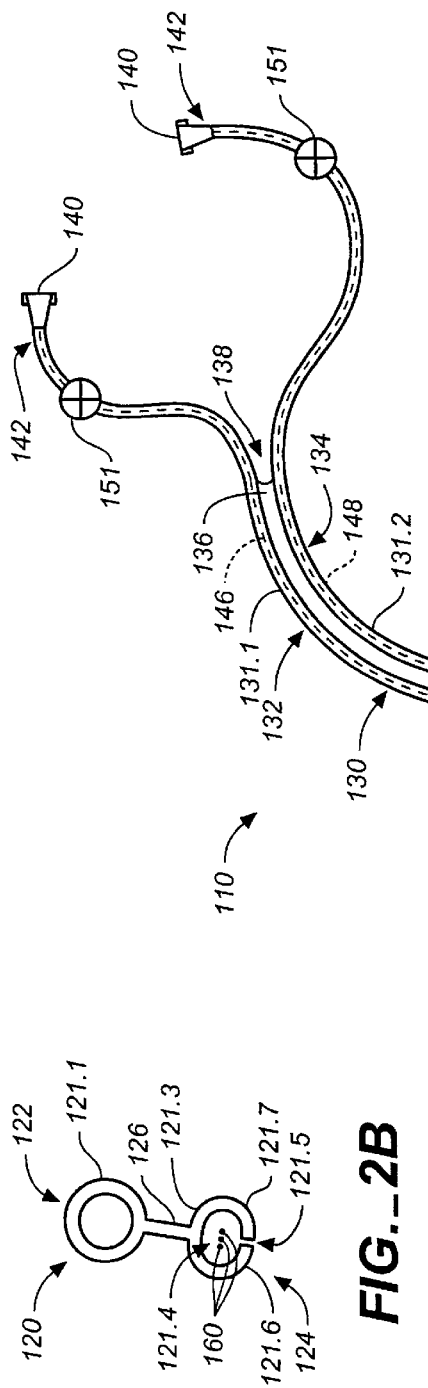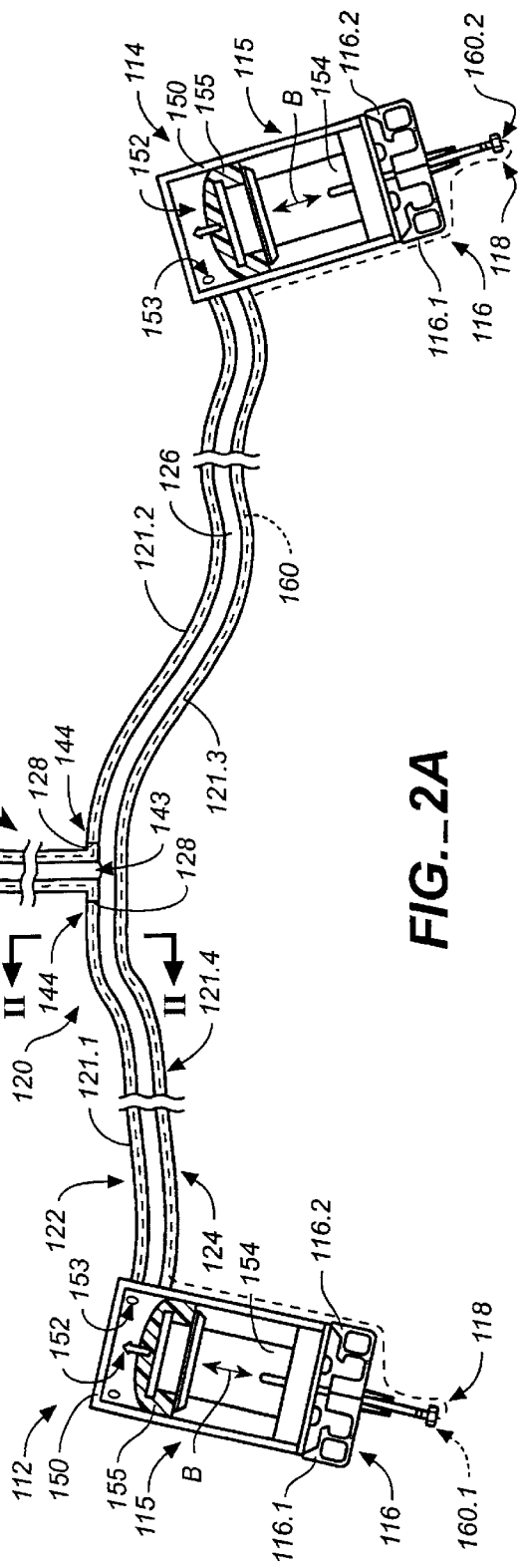

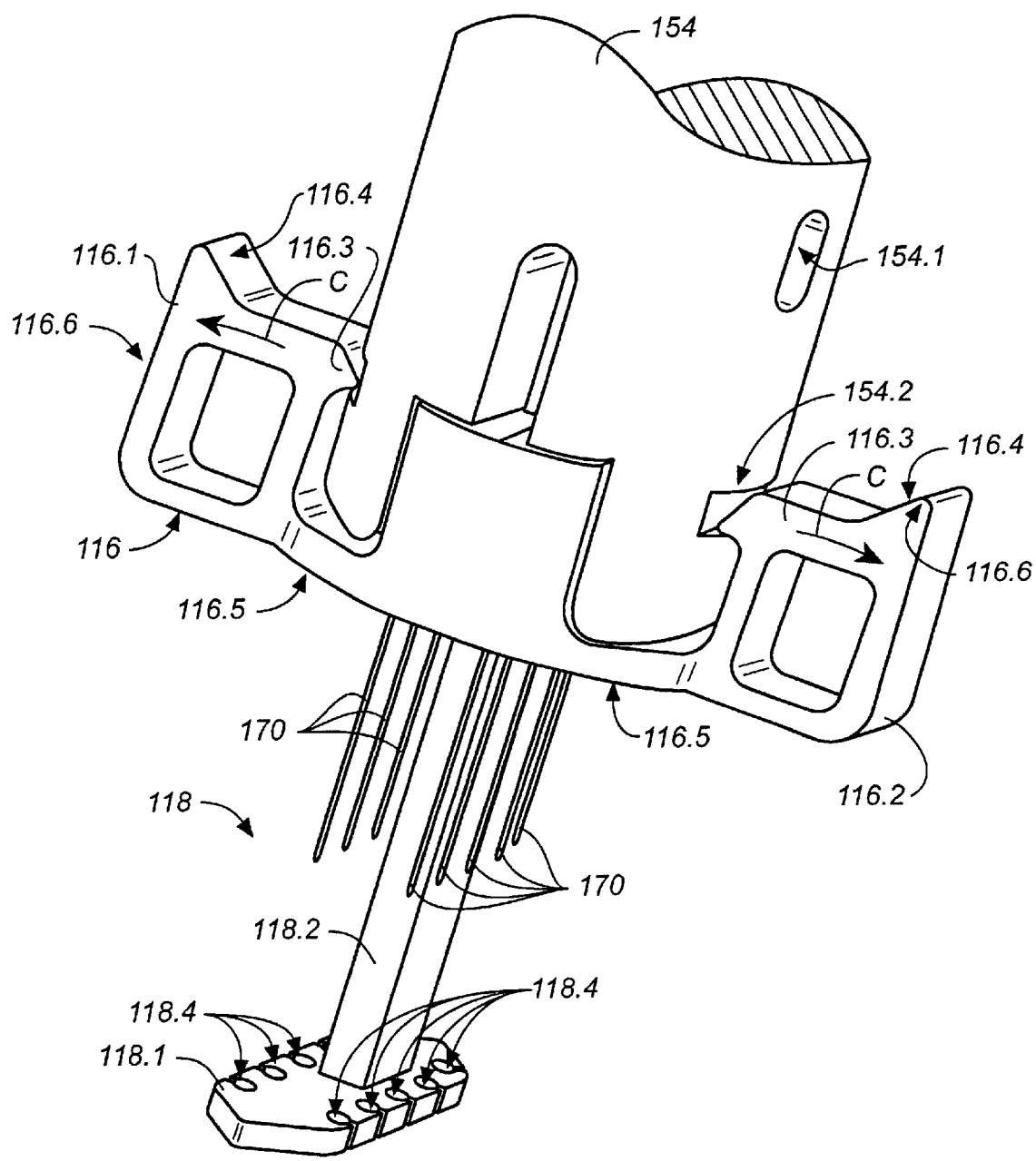
FIG._3

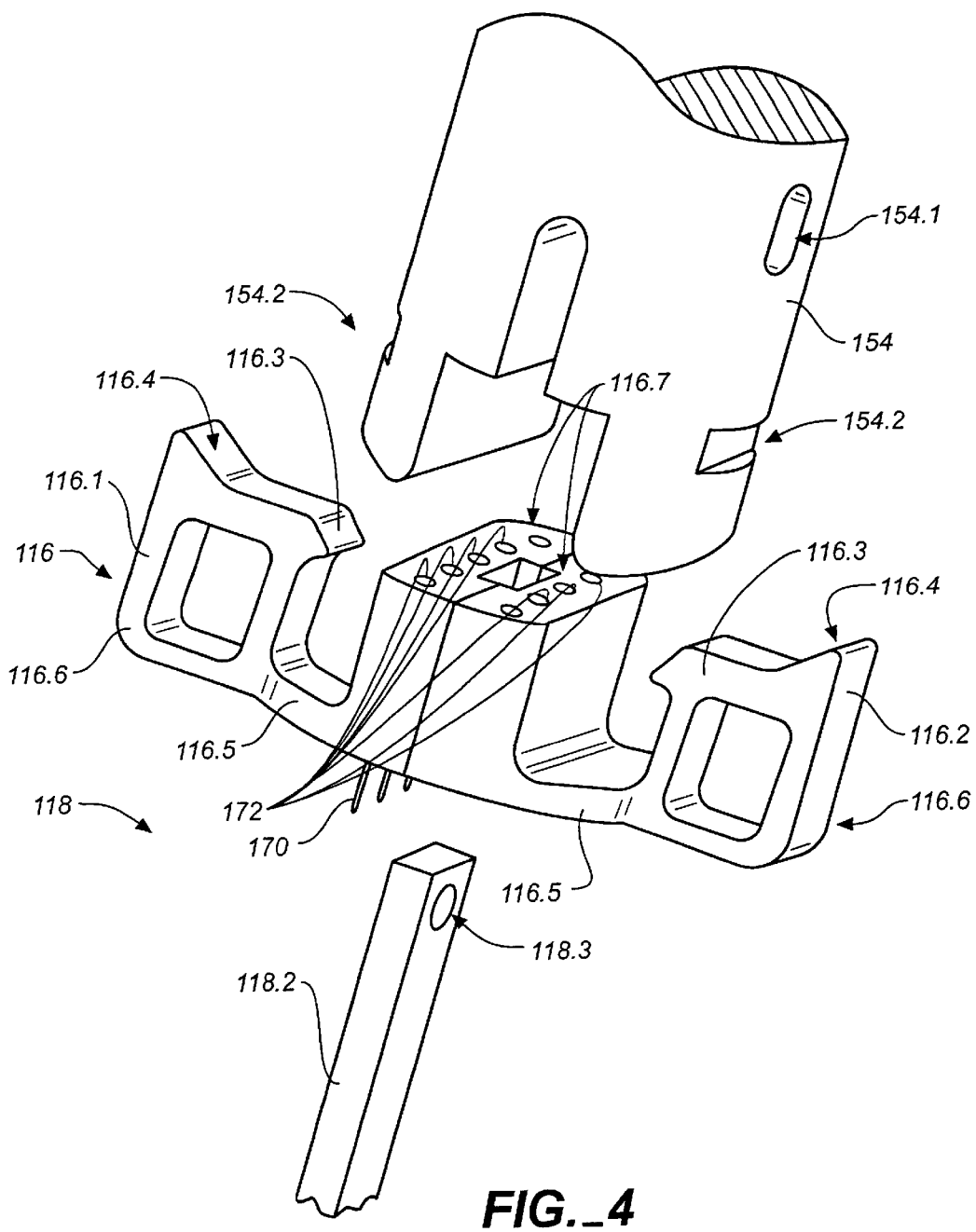
FIG._4

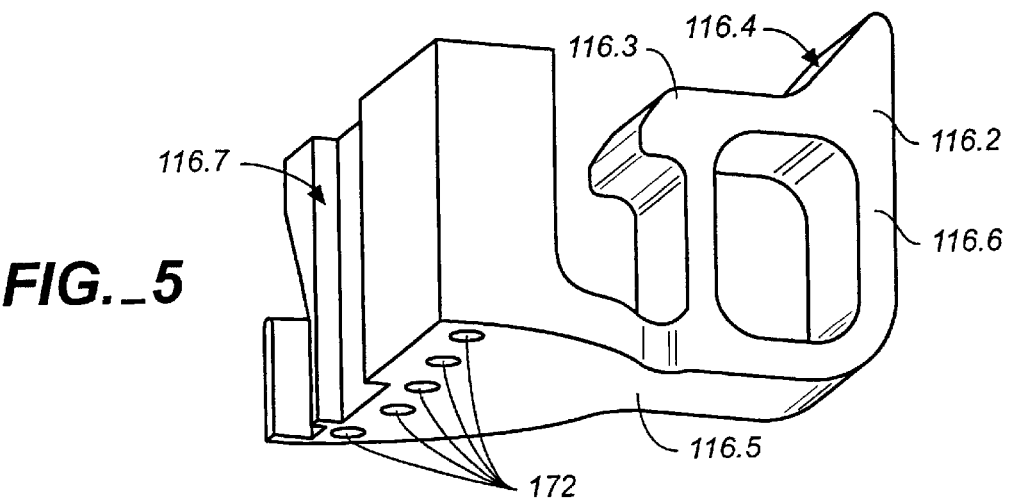
FIG._5
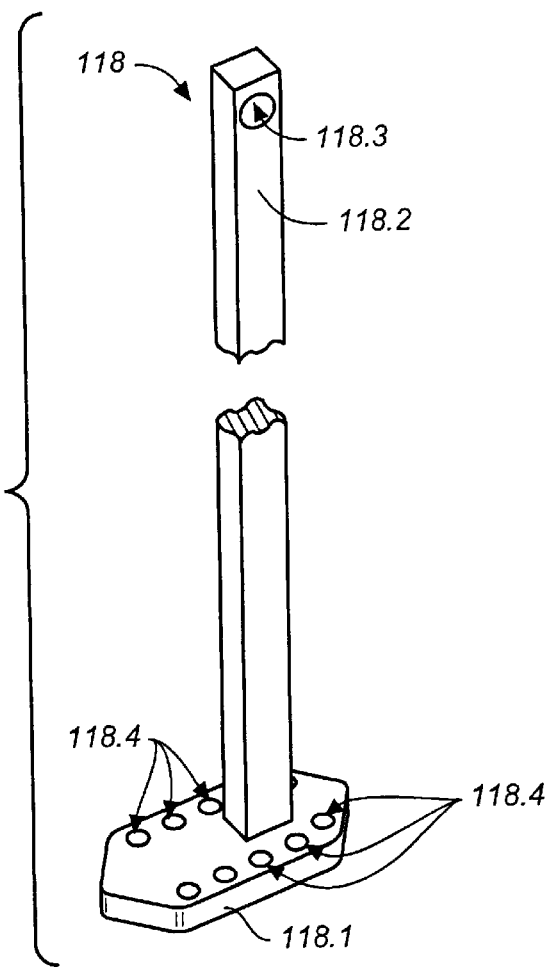
FIG._6

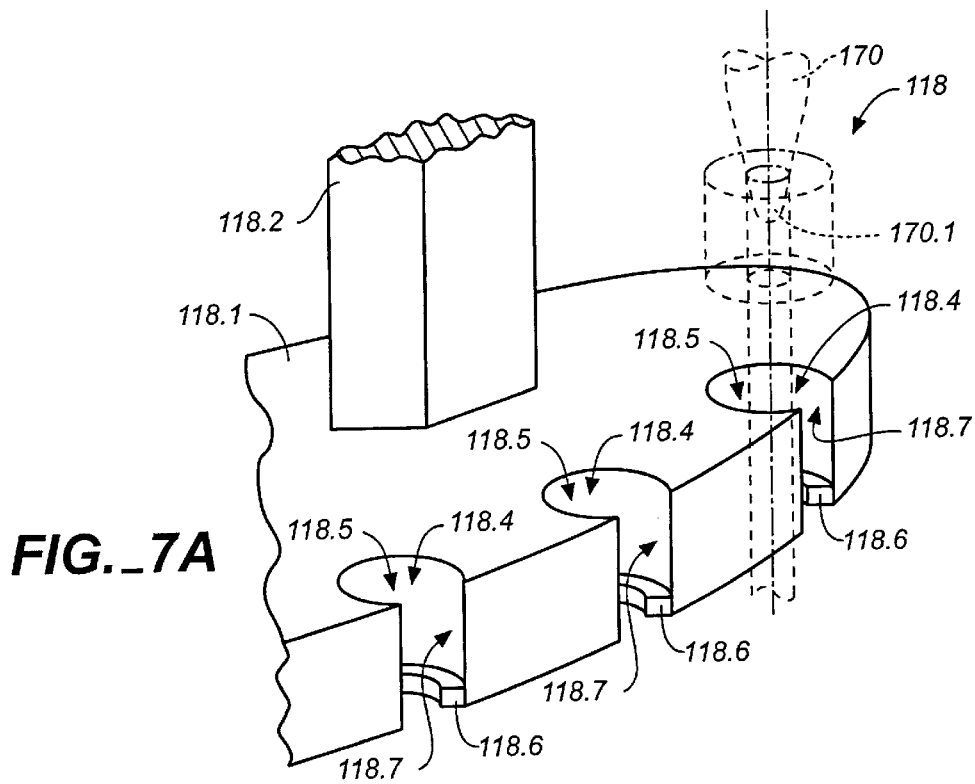
FIG._7A
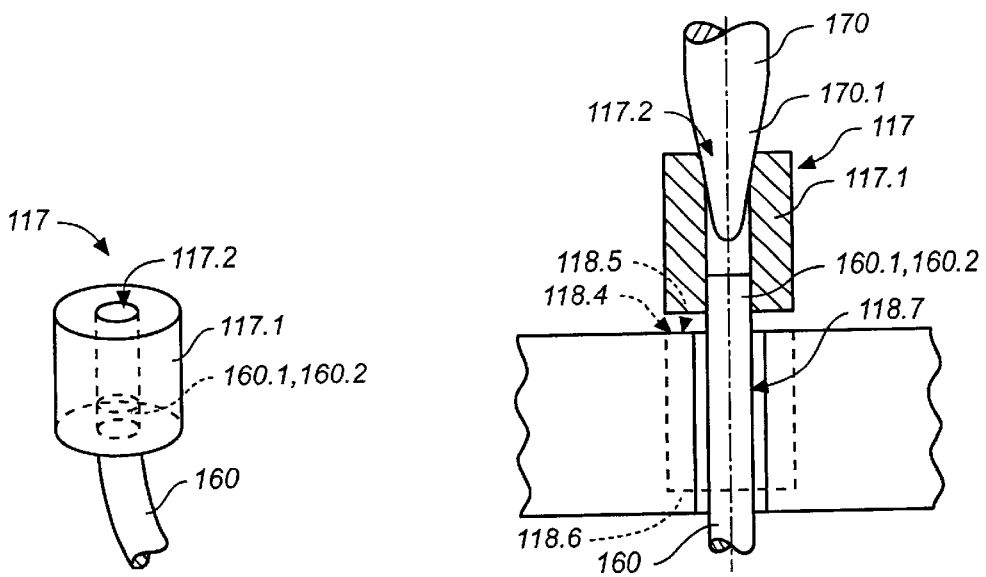
FIG._7B  FIG._7C

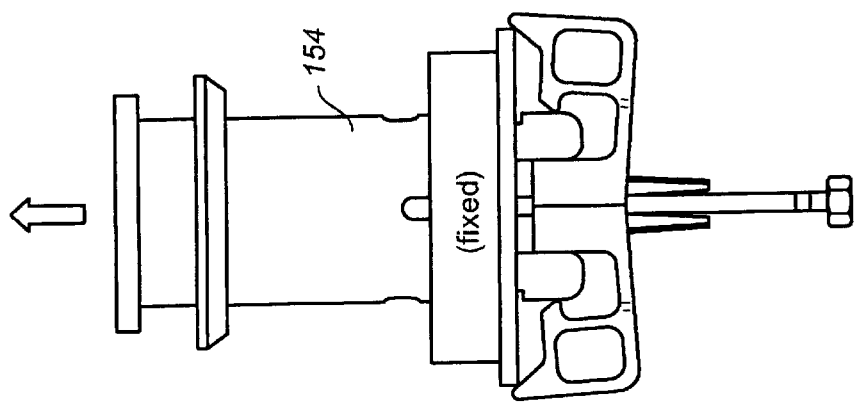
FIG._8C
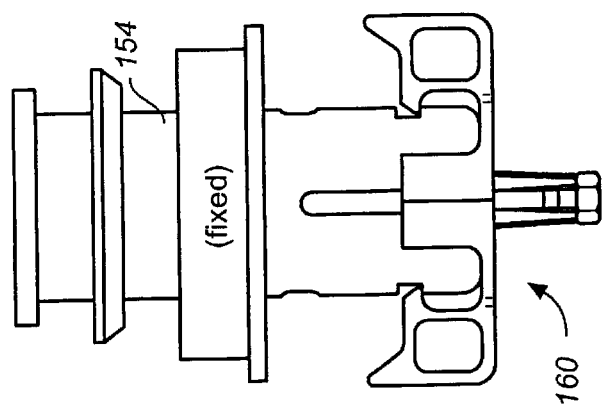
FIG._8B
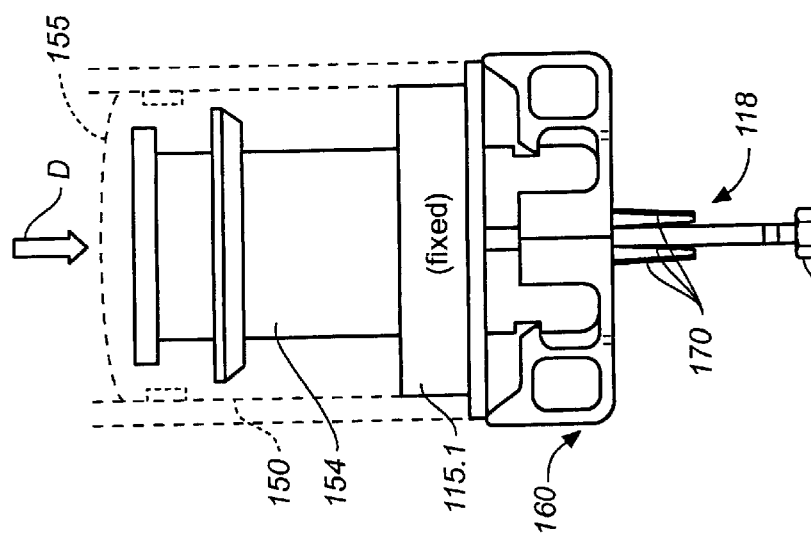
FIG._8A

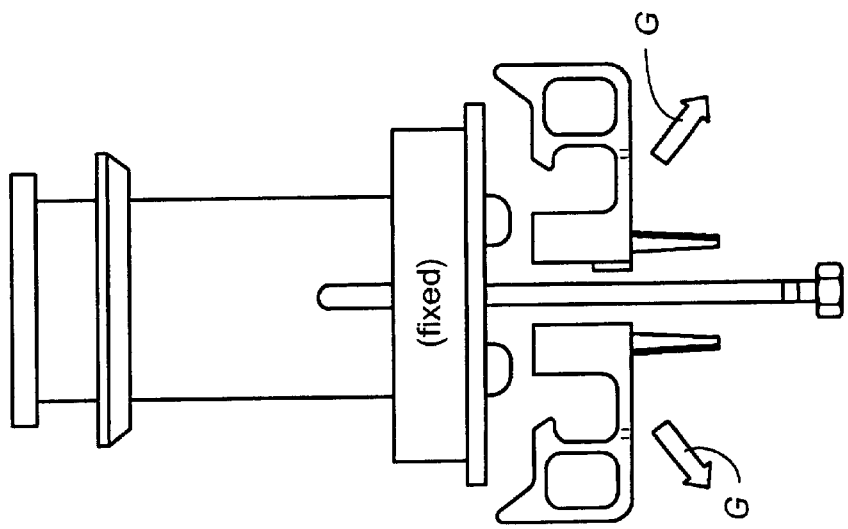
FIG._8E
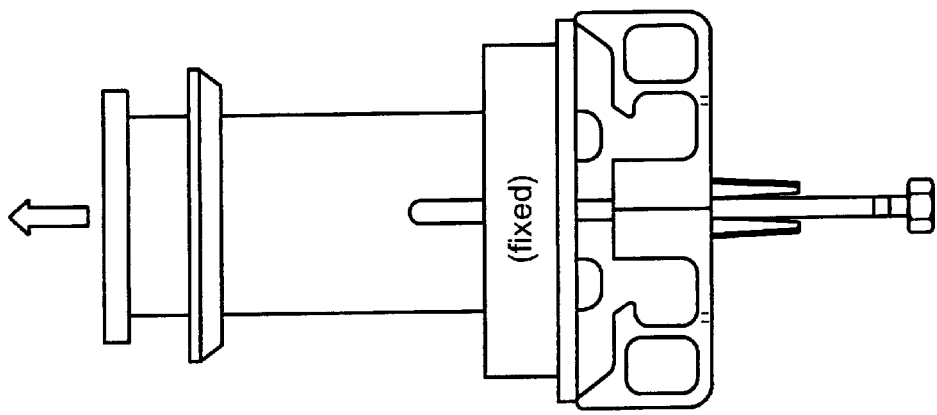
FIG._8D

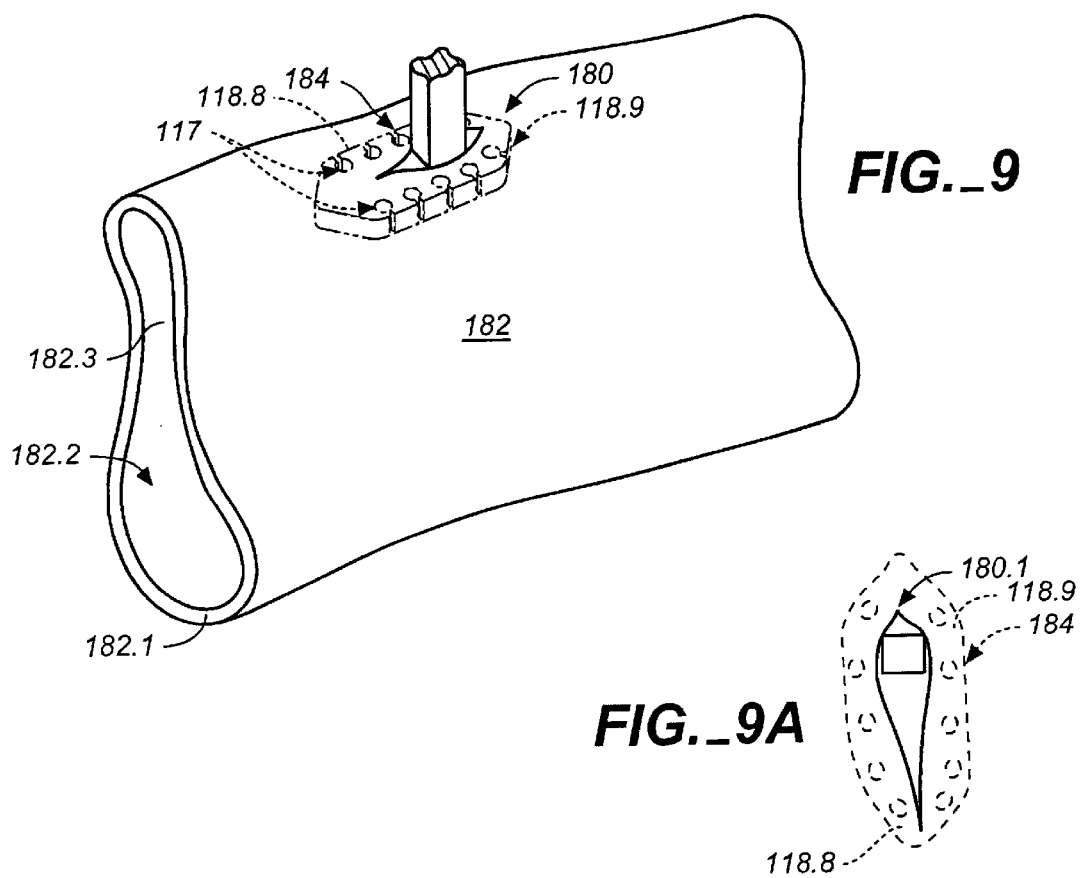
FIG._9
FIG._9A
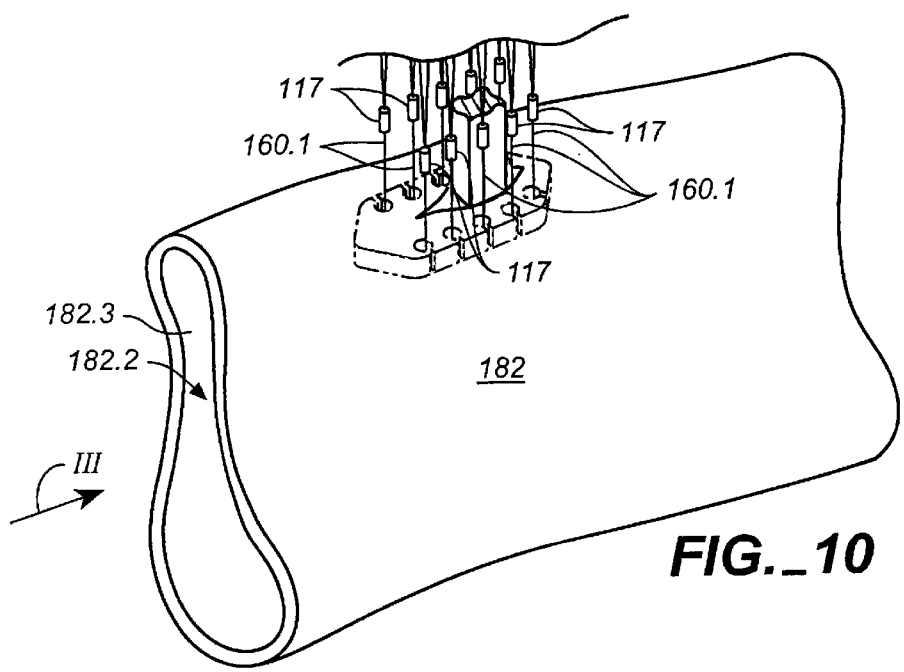
FIG._10

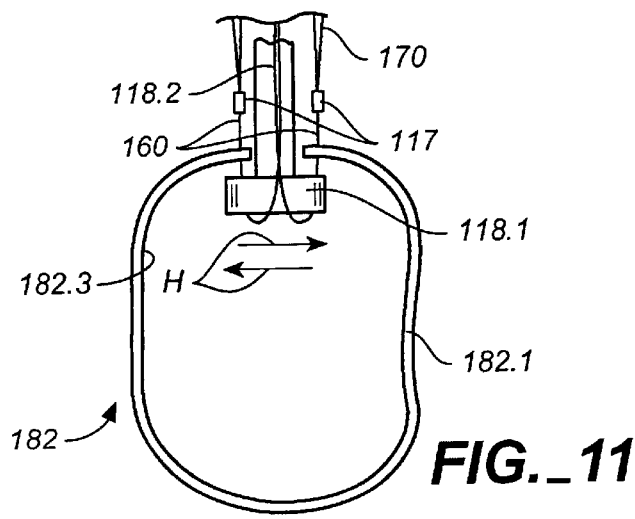
FIG._11
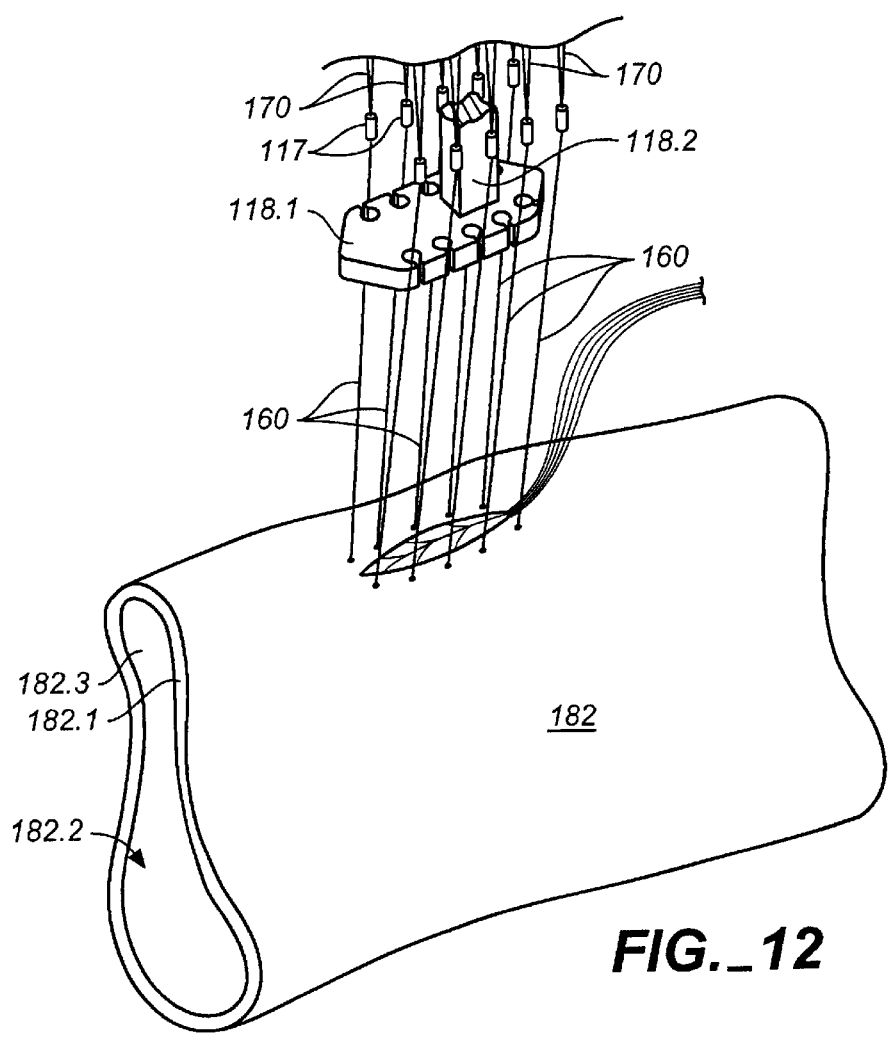
FIG._12

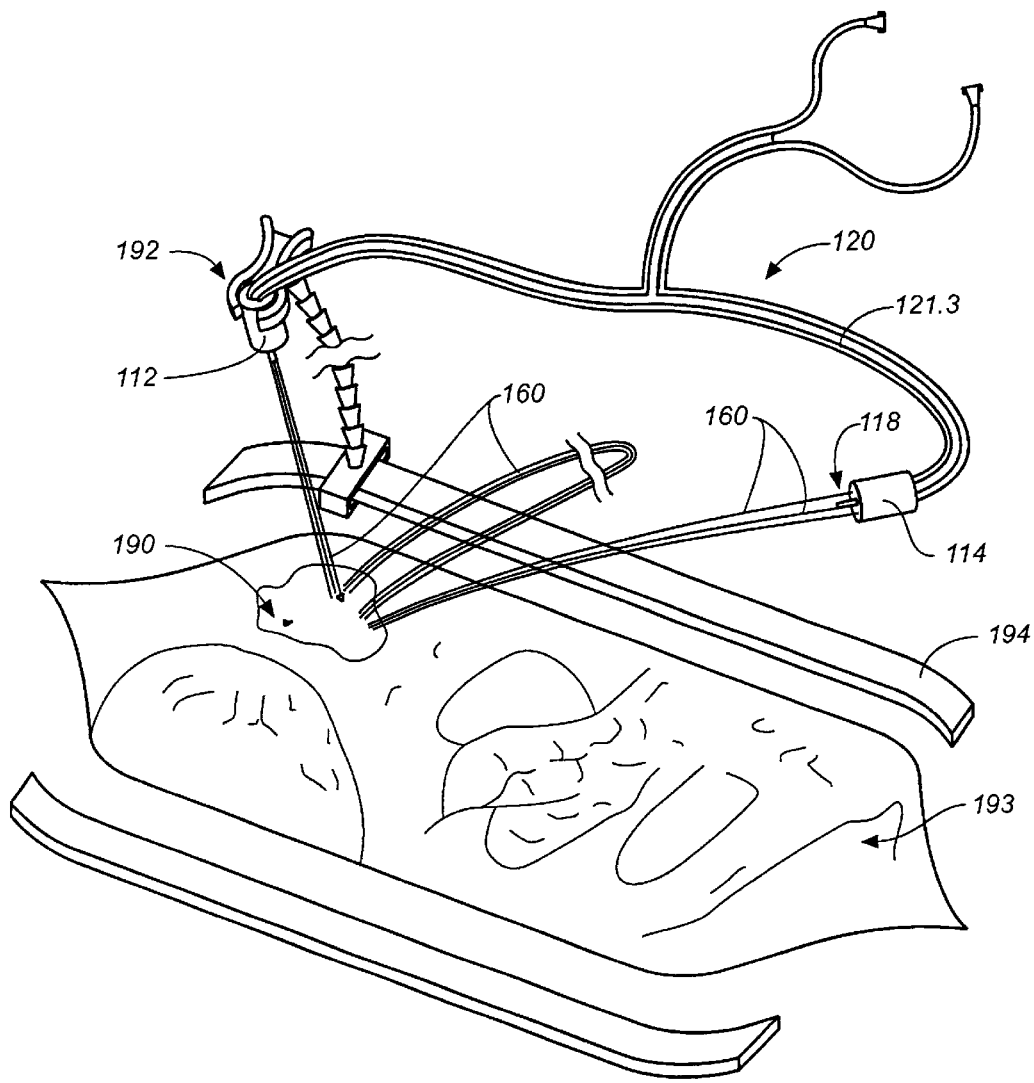
FIG._13

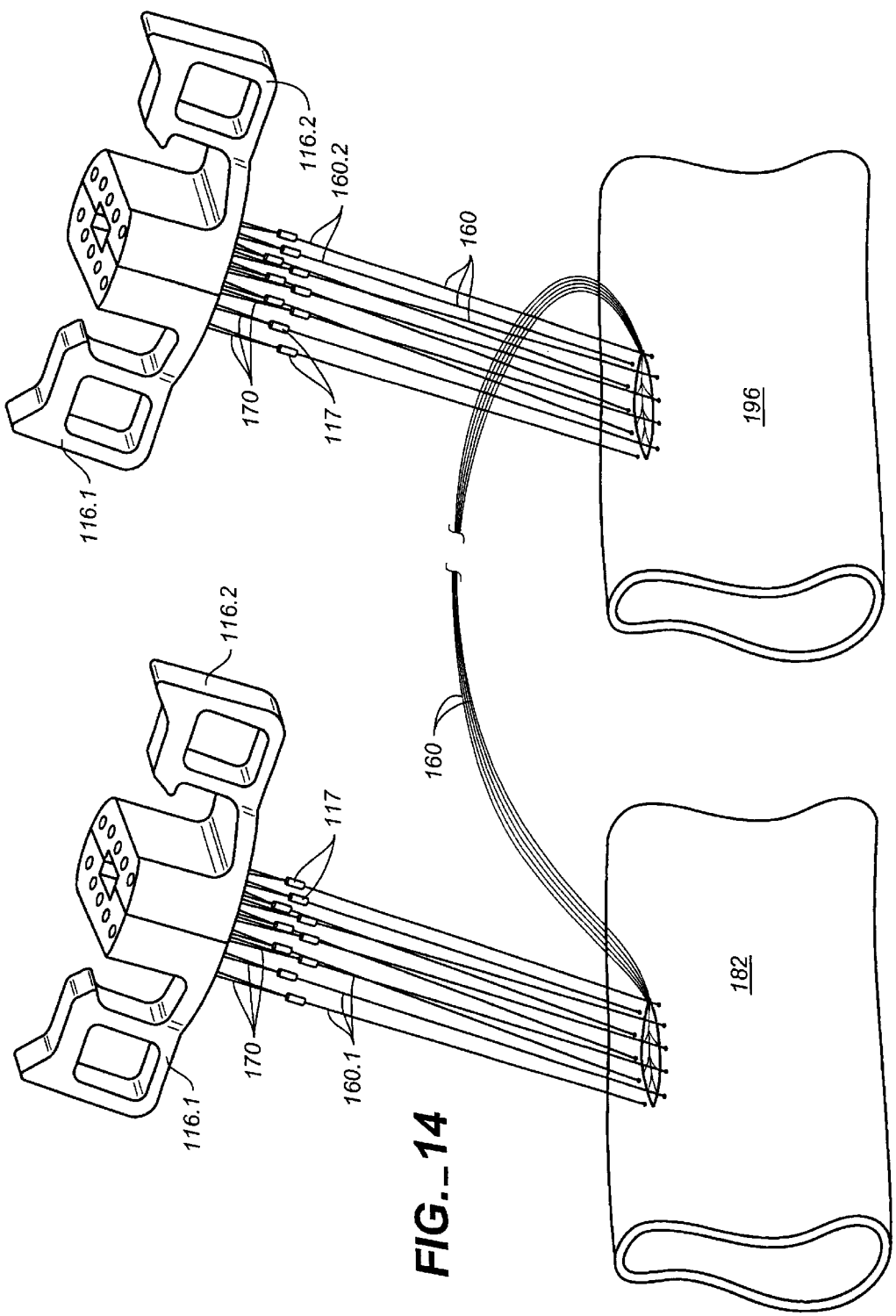
FIG._14

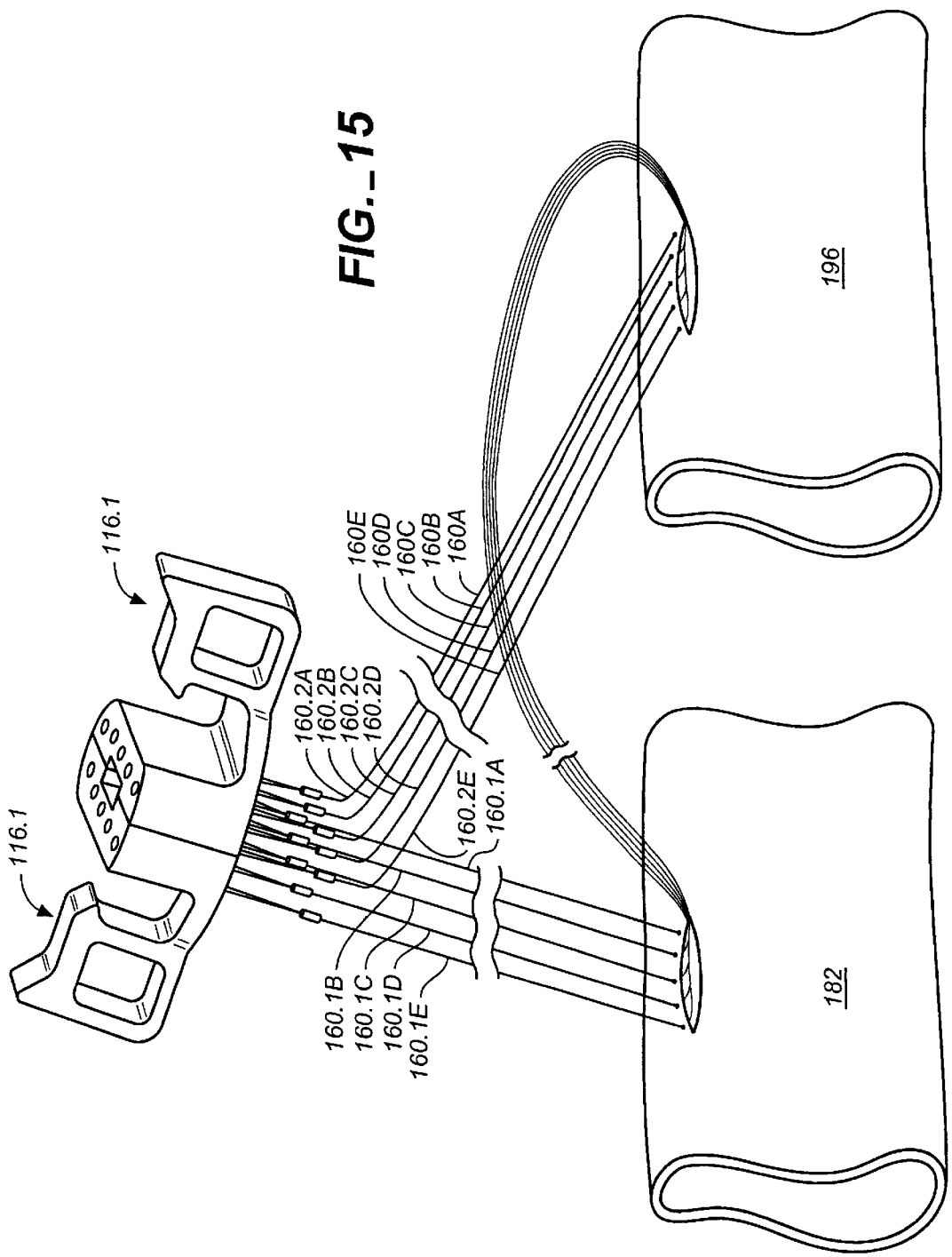

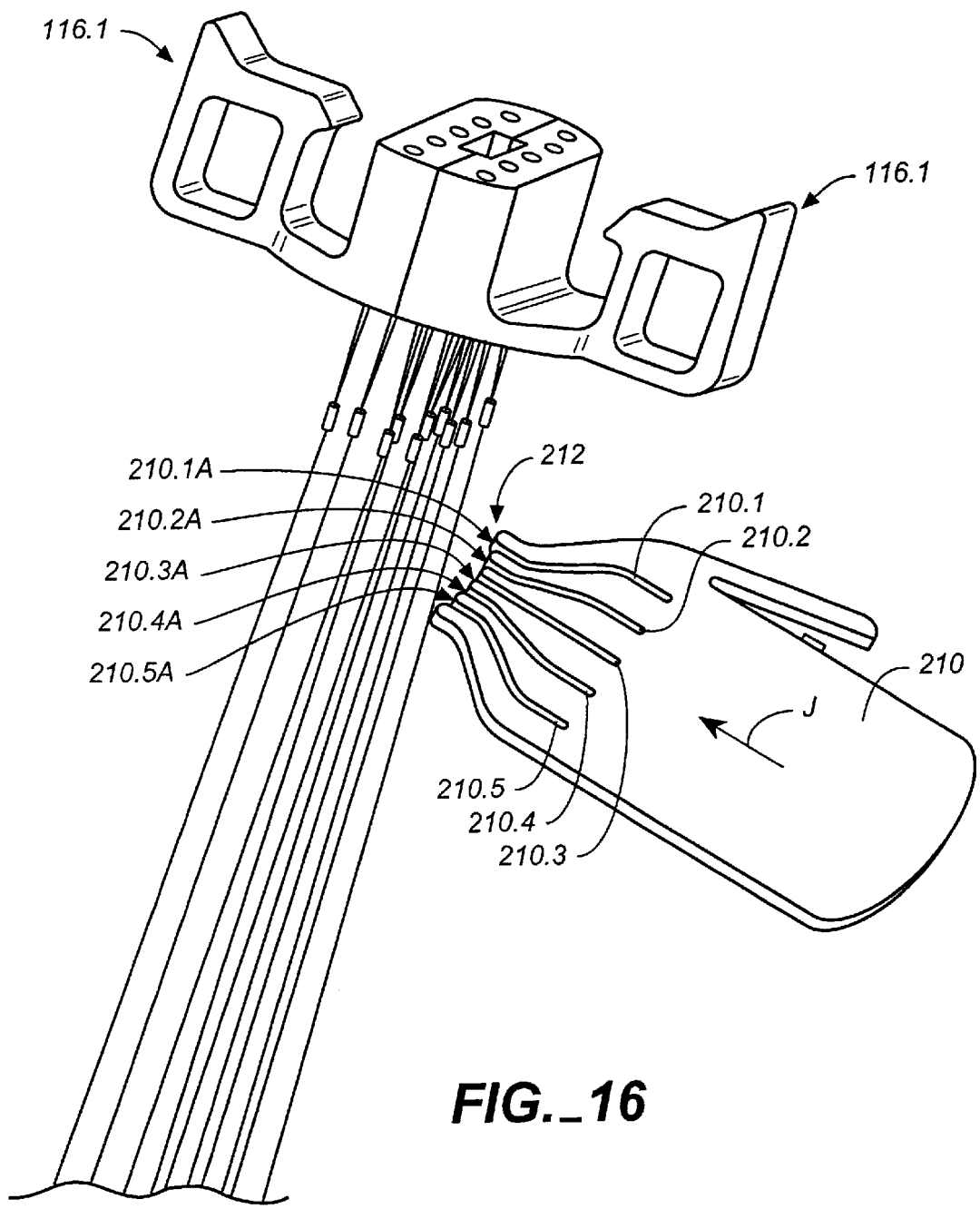
FIG._16

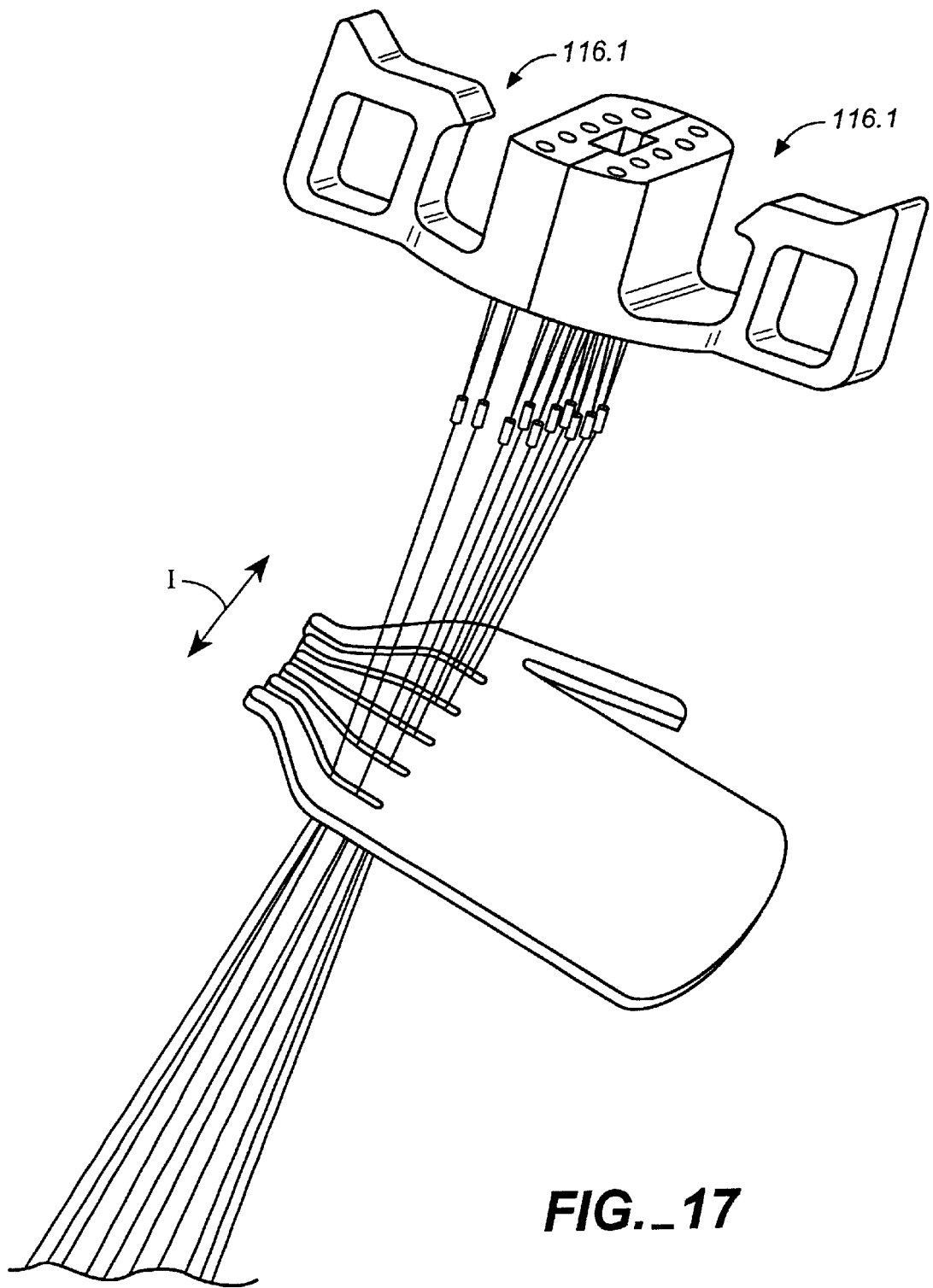
FIG._17

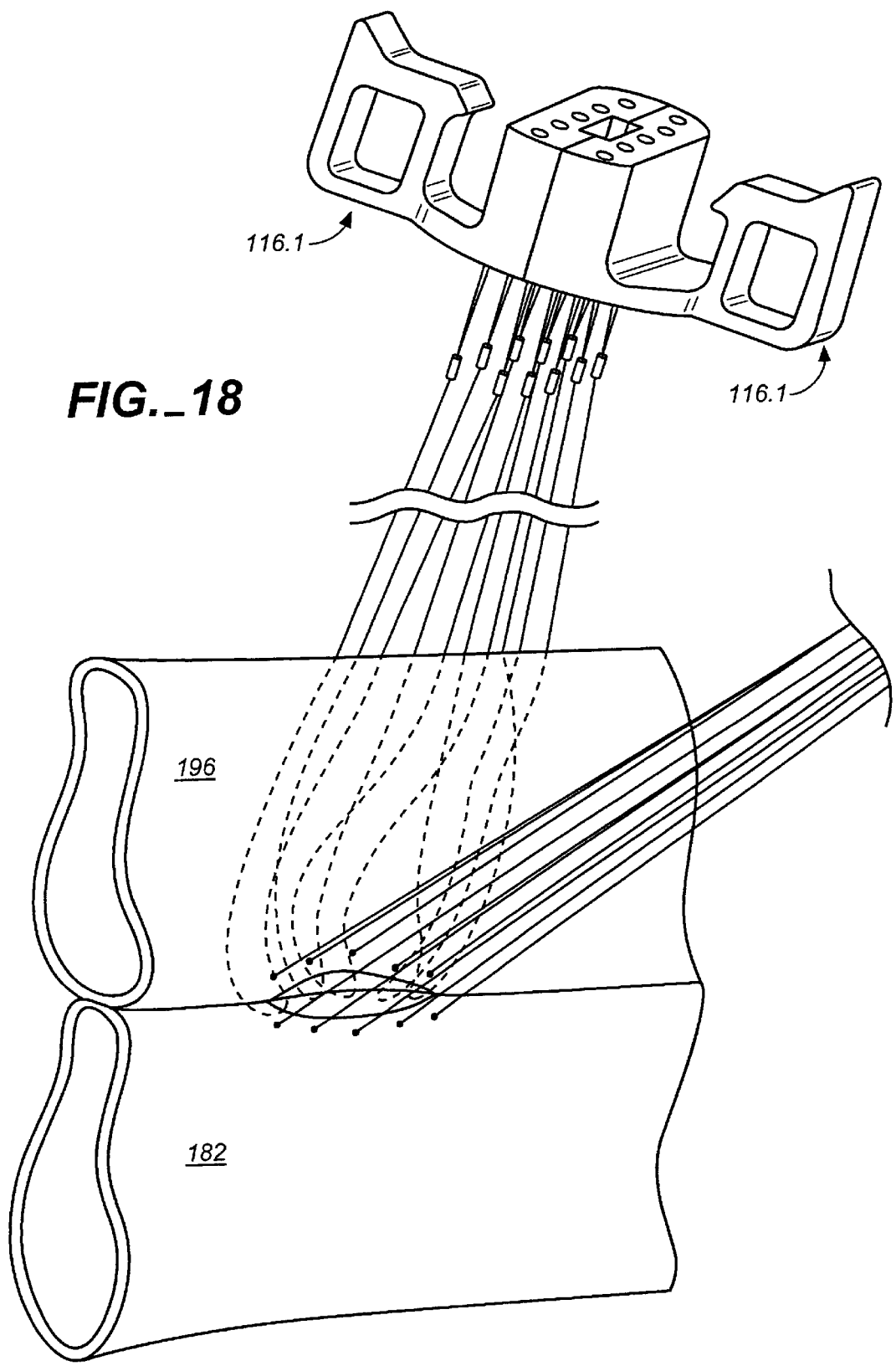
FIG._18

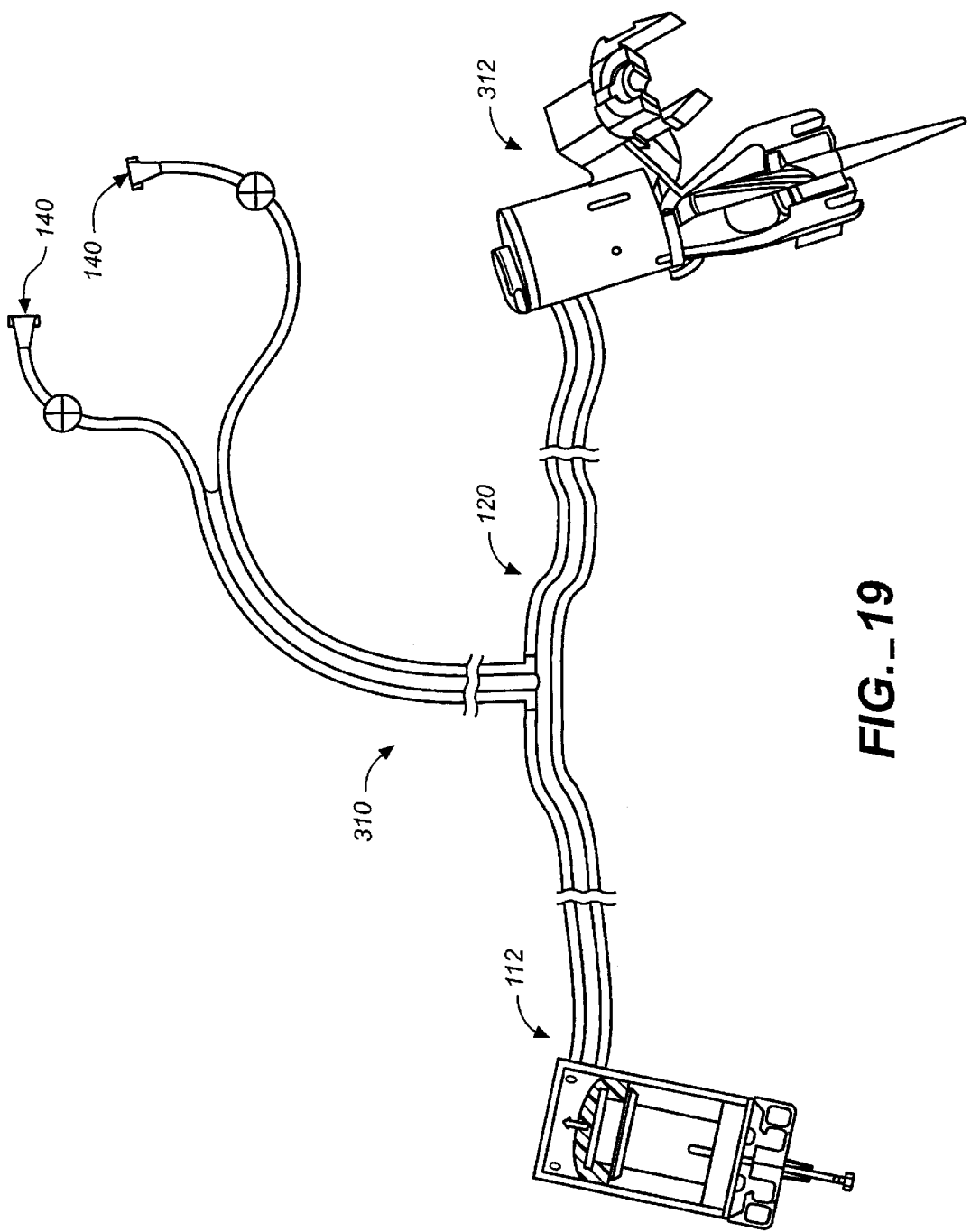
FIG._19

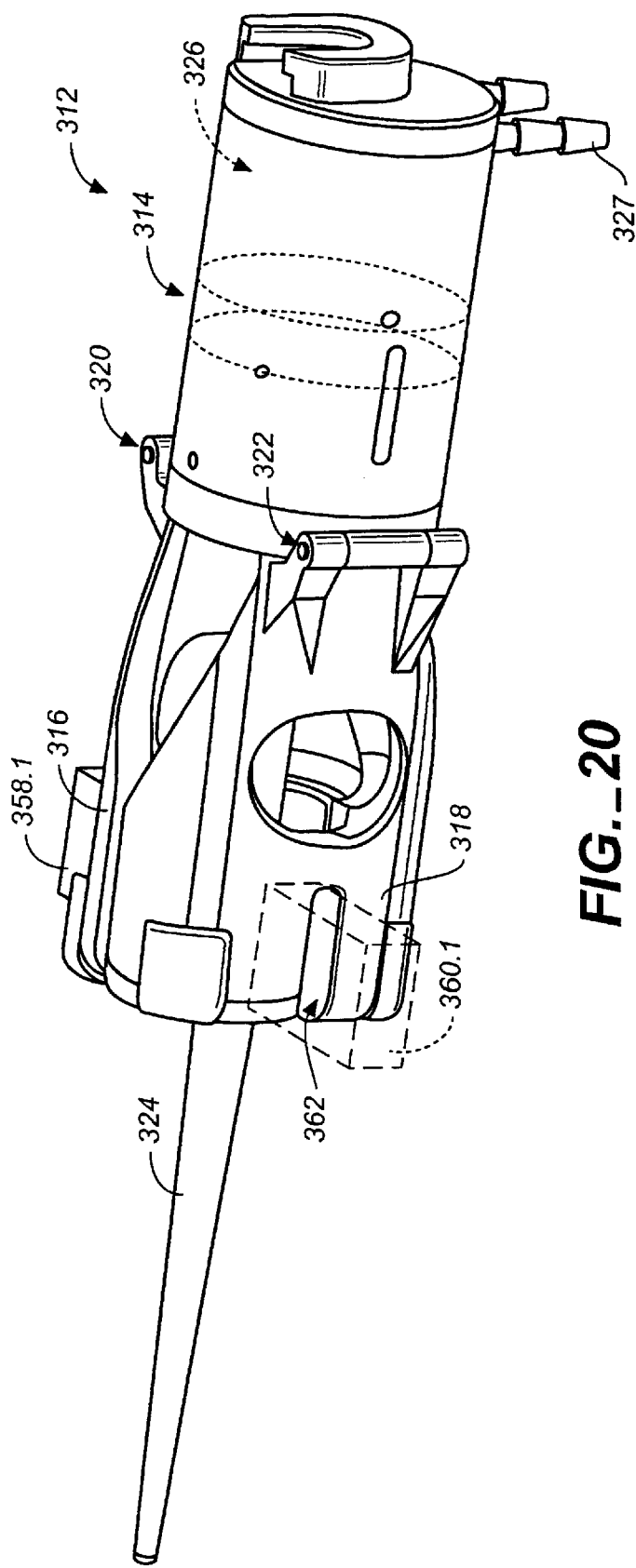
FIG._20

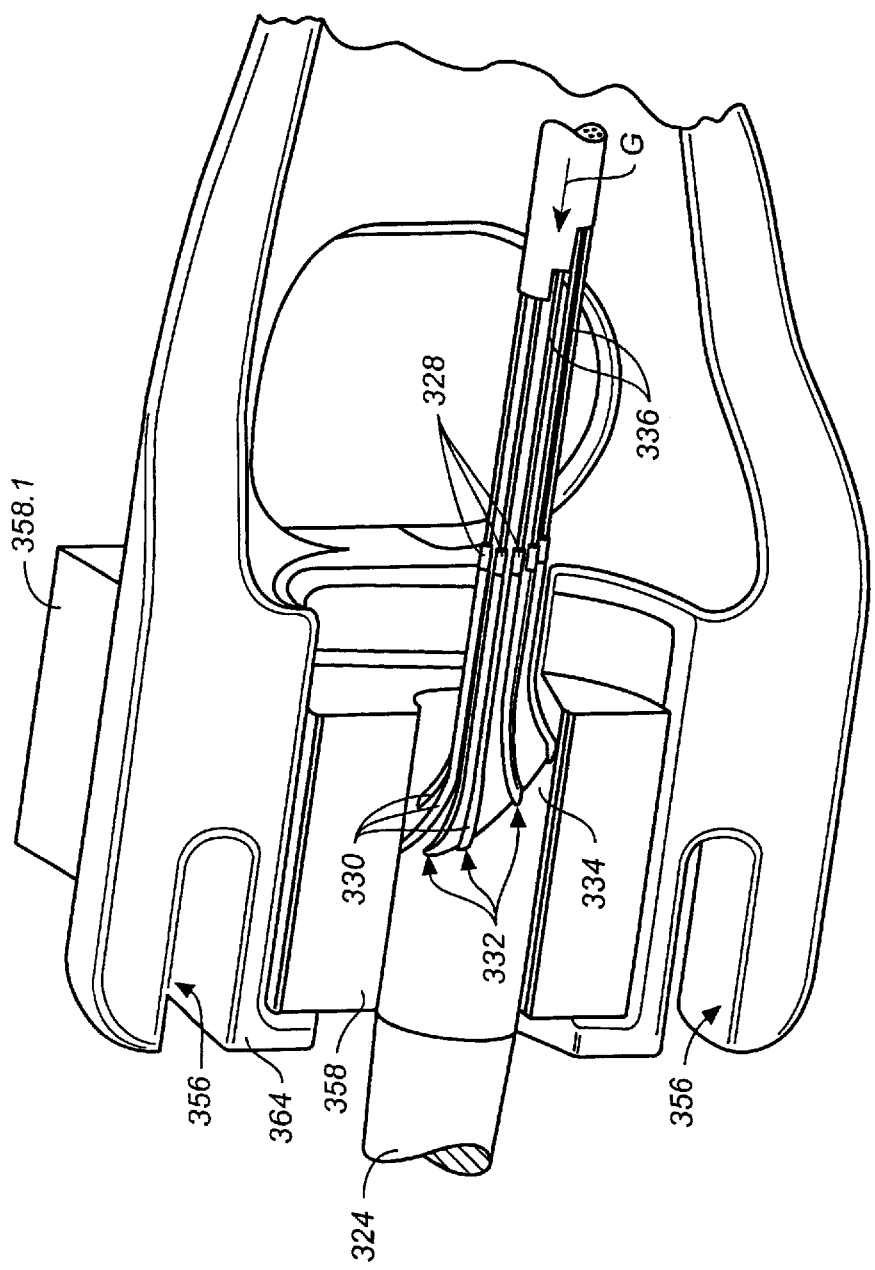
FIG._21

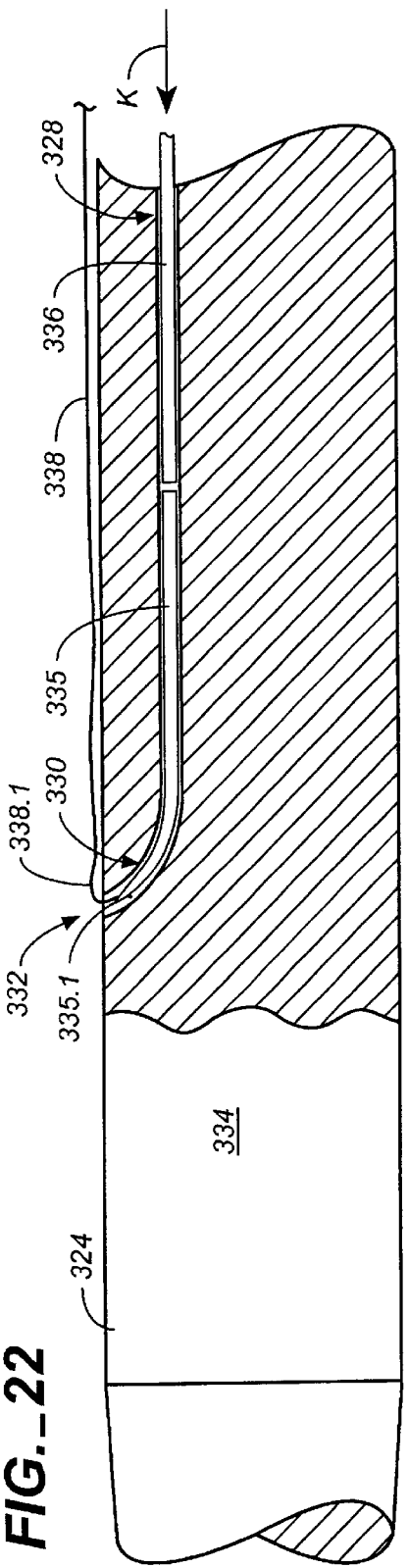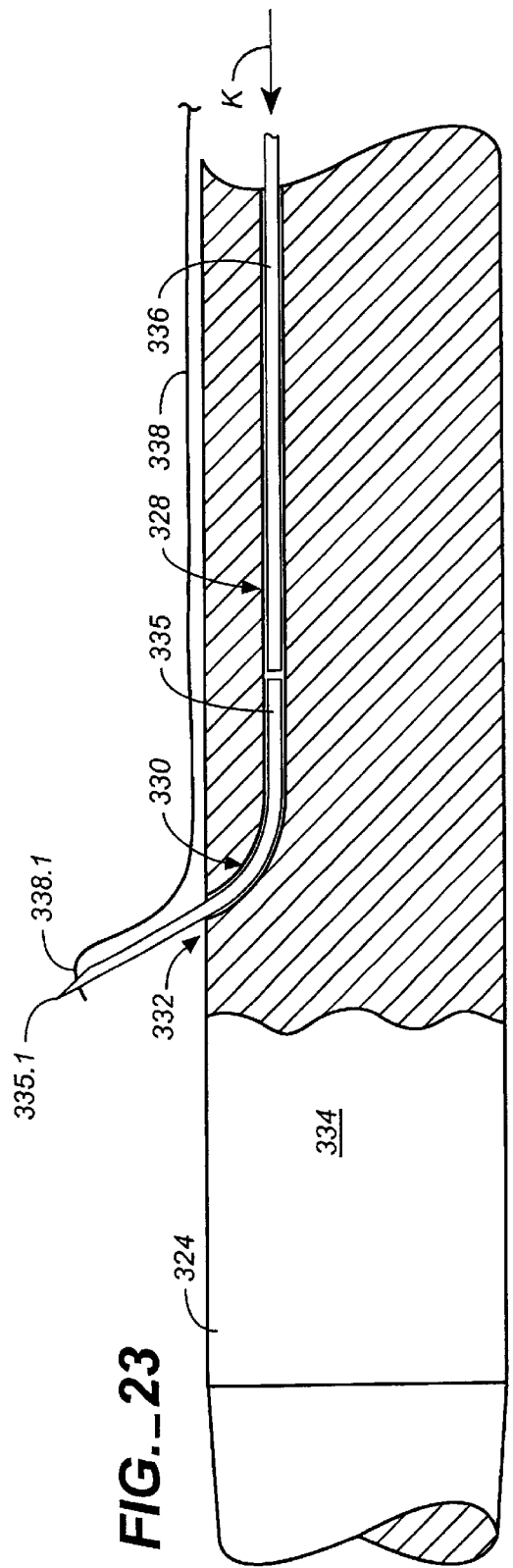

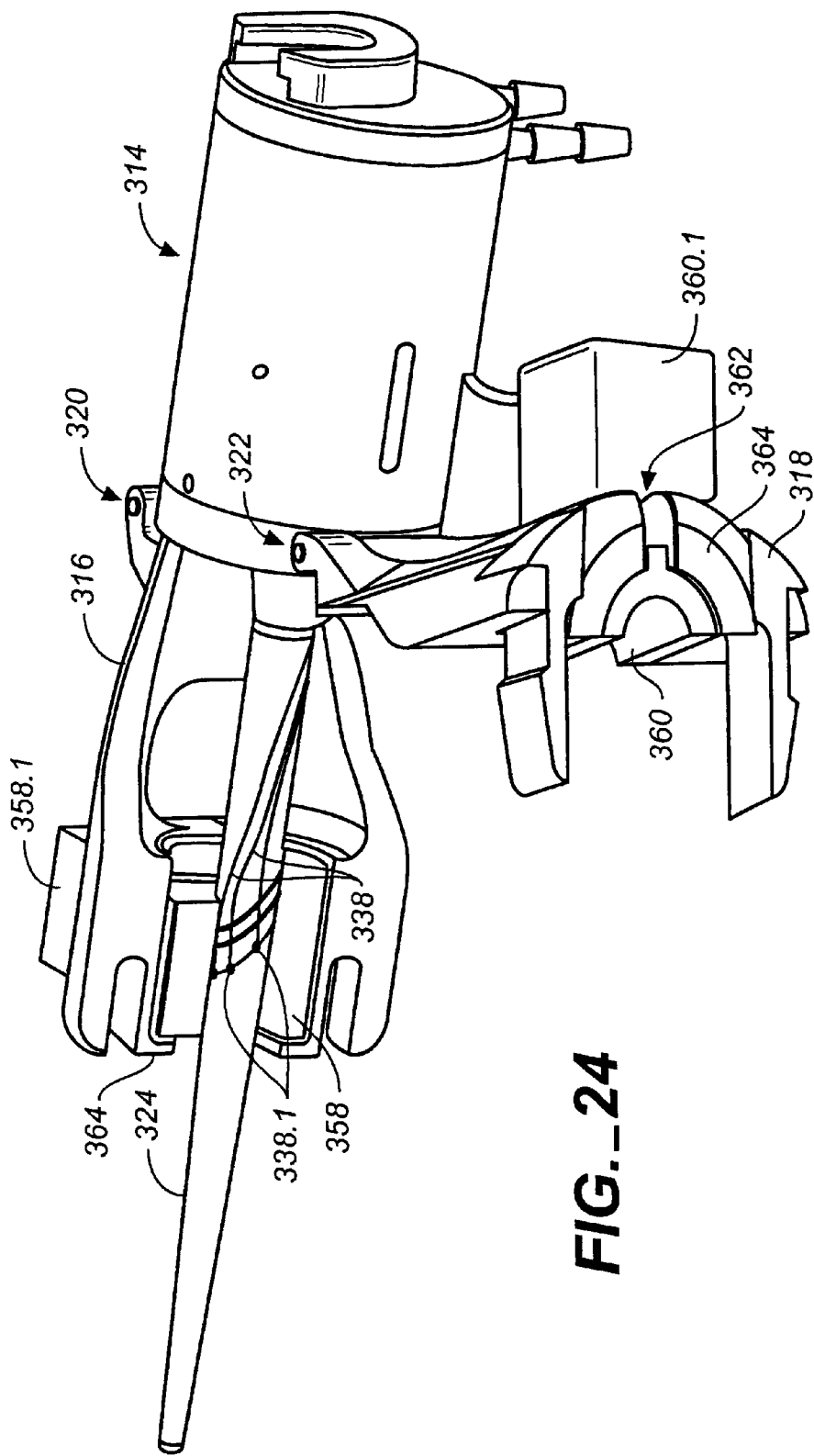
FIG._24

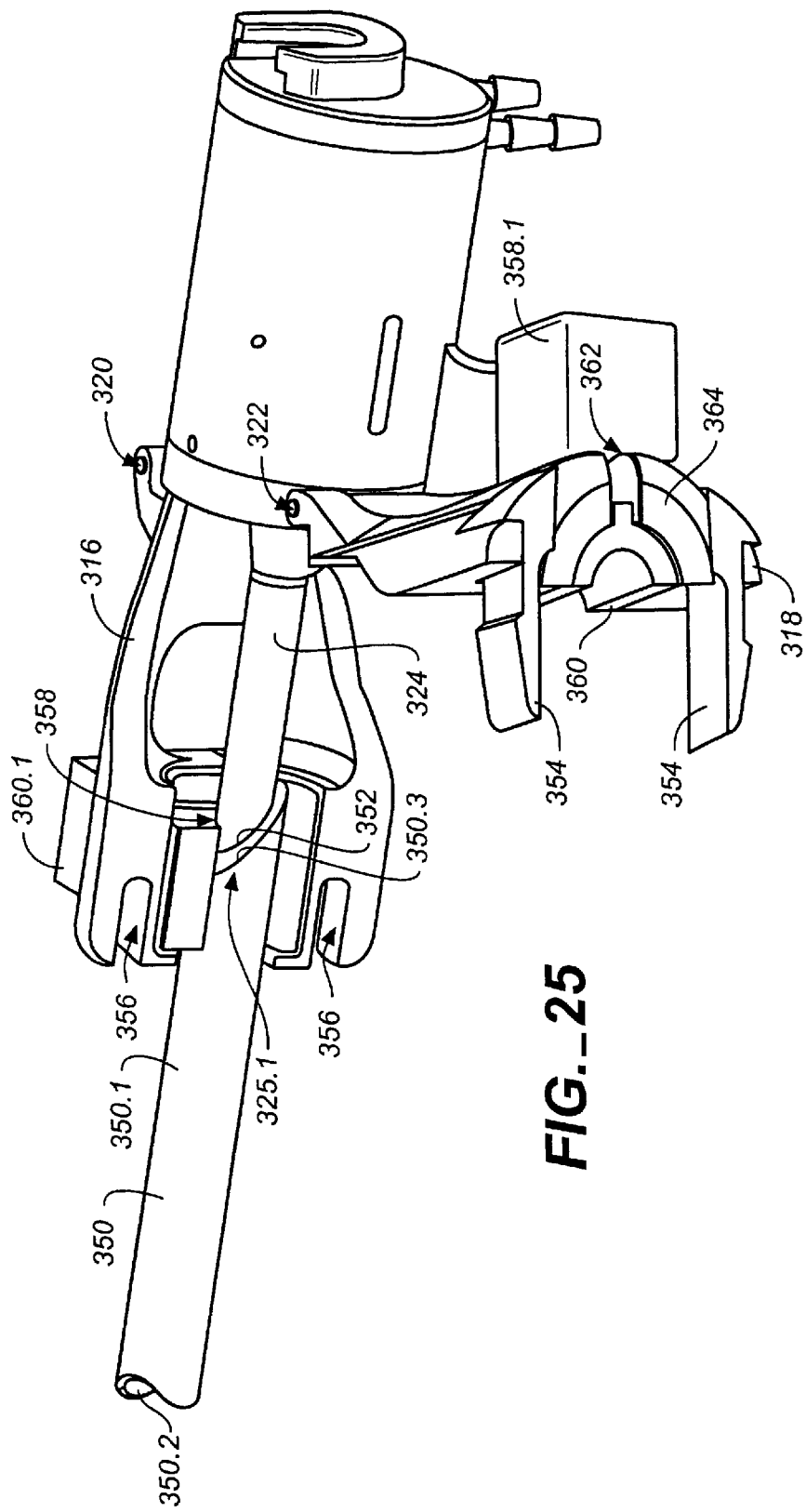
FIG._25

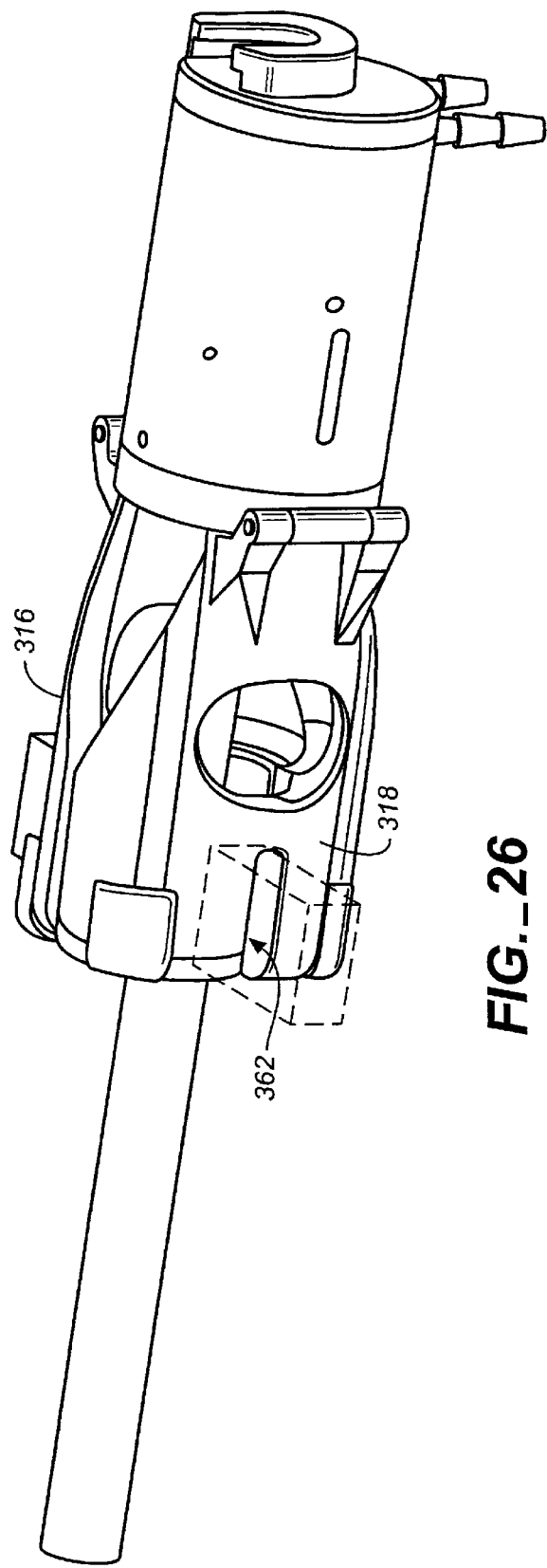
FIG._26

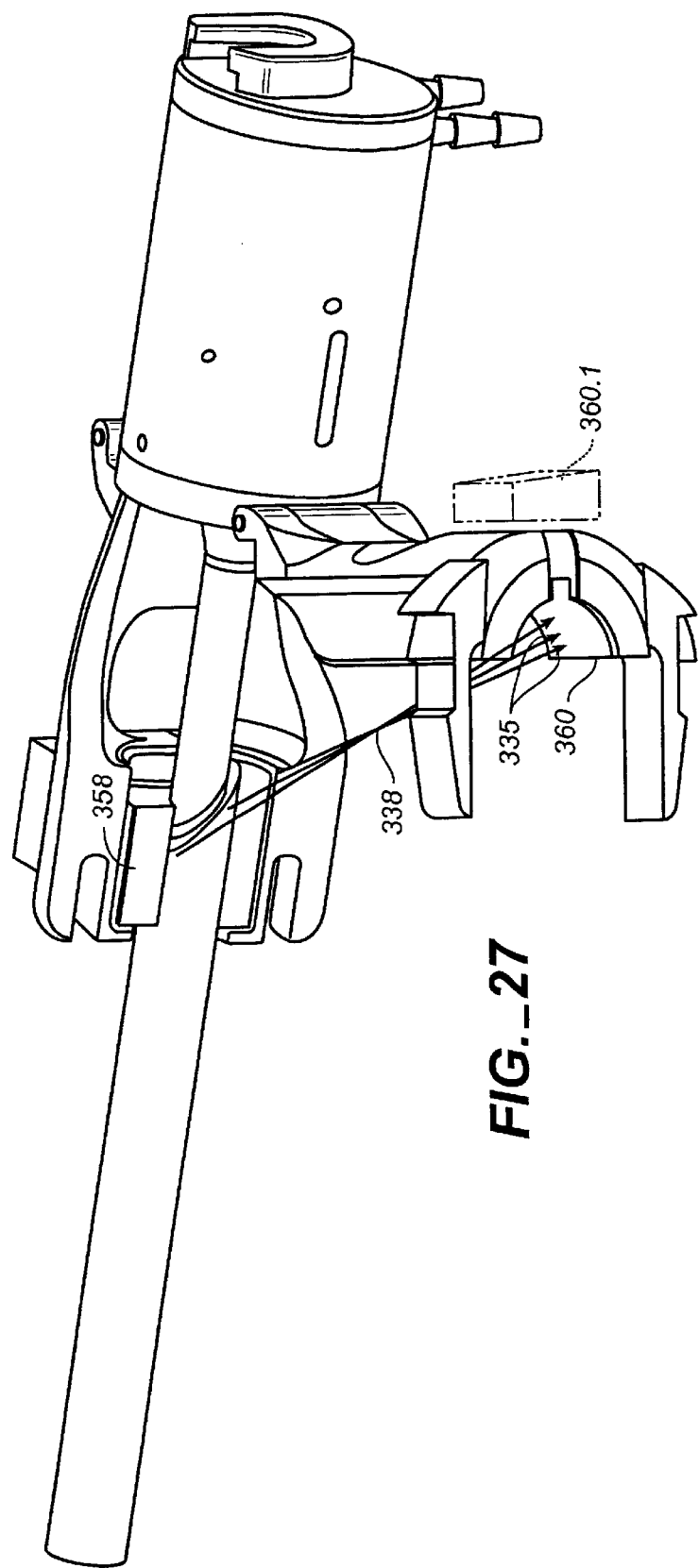
FIG._27

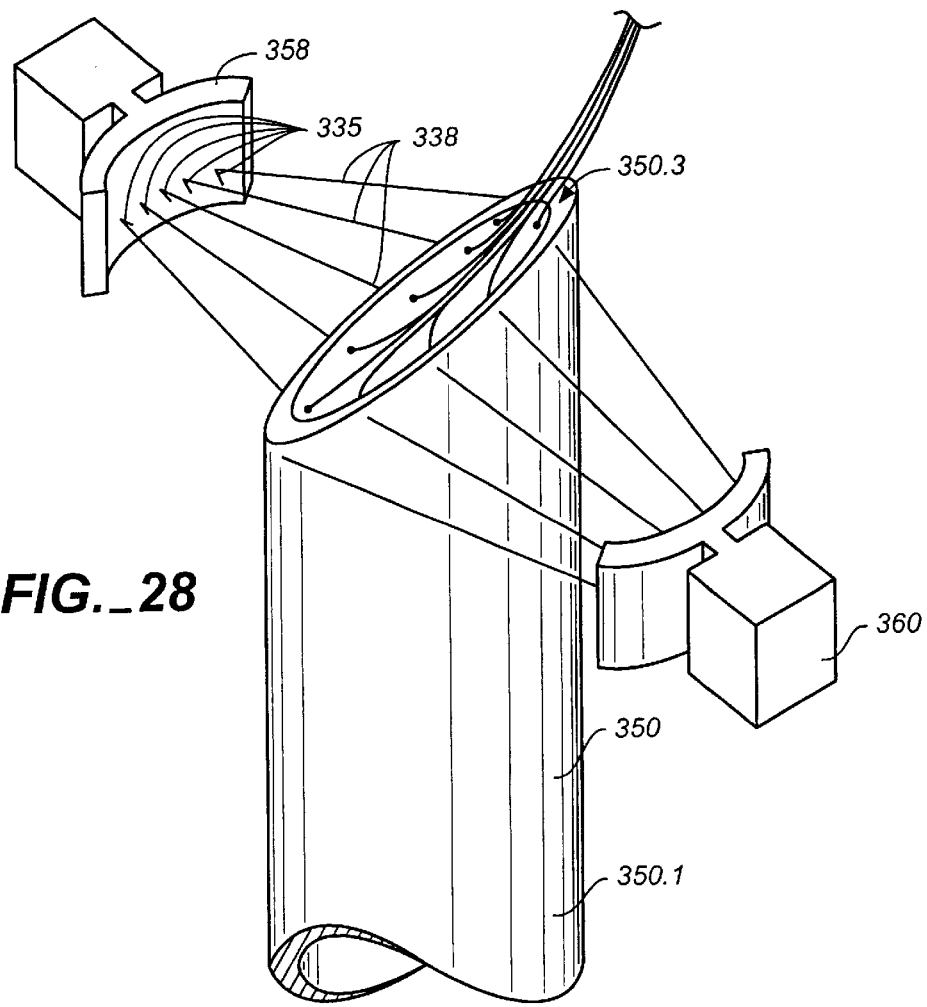
FIG._28
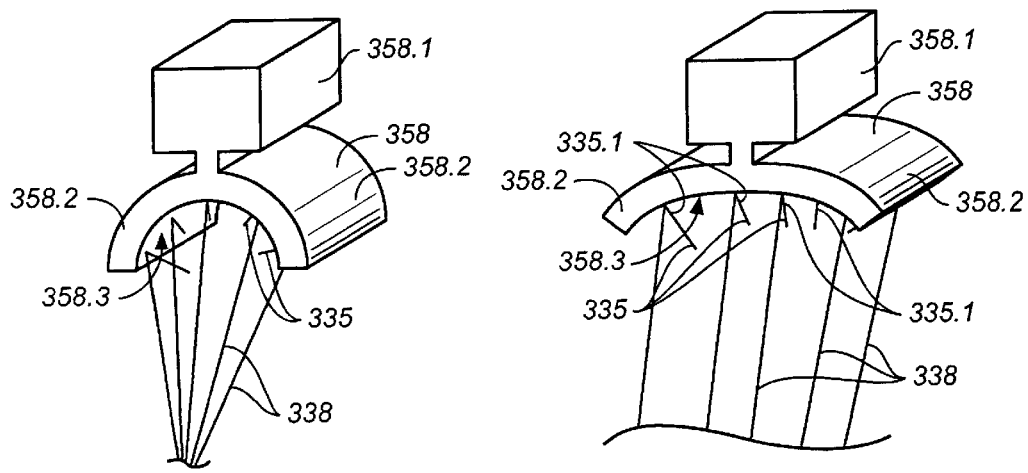
FIG._28A  FIG._28B

SYSTEMS, DEVICES AND METHODS FOR DEPLOYING NEEDLES

CROSS-REFERENCES TO RELATED APPLICATIONS

This application is related to commonly assigned, copending U.S. patent application Ser. No. 08/824,031 filed on Mar. 26, 1997, U.S. Pat. No. 6,036,699 patent application Ser. No. 08/883,246 filed on Jun. 26, 1997, U.S. Pat. No. 6,355,050 patent application Ser. No. 08/638,076 filed on Apr. 26, 1996, U.S. Pat. No. 5,792,152 and patent application Ser. No. 09/395,901 entitled "Device and Method for Performing End-to-Site Anastomosis," filed on Sep. 14, 1999, U.S. Pat. No. 6,358,258. Furthermore, this application is related to patent application Ser. No. 09/610,564 filed on Jun. 30, 2000, patent application Ser. No. 09/610,099 filed on Jun. 30, 2000 and patent application Ser. No. 09/608,832 filed on Jun. 30, 2000. The full disclosure of each of the above applications is incorporated herein by reference.

FIELD OF THE INVENTION

This invention relates to actuating medical devices. In particular, the invention relates to a needle deployment device and to a method of performing a medical procedure.

BACKGROUND OF THE INVENTION

The invention can be used advantageously in the field of placing suture elements at a surgical site. Accordingly, the invention can be used in the field of suturing vessels, ducts, and the like, in a patient body. The invention can be used in the field of forming sutures in bowel connections, femoral-popliteal artery anastomoses, and the like. It can also be used in the field of trauma closure, and the like. The invention can be used particularly advantageously in the field of suturing blood vessels together during cardiac surgery, for example. Accordingly, the invention can be used during coronary artery bypass graft surgery (CABG), and the like. However, it is to be appreciated that the field of the invention is not to be limited to such uses only, but extends to actuating medical devices in general.

It is often required to connect a vessel, duct, or the like, such as a hollow organ, or blood vessel, or the like, to a target piece of tissue, such as another vessel, duct, or the like. This is especially true in the case of certain types of cardiac surgery, such as CABG surgery. Often during such CABG surgery it is required to connect, or join, one blood vessel to another so that the vessels are joined together to be in fluid flow communication with each other. A joint formed between blood vessels in this fashion is often referred to as an anastomosis.

As is well known, the heart pumps blood through the body. The heart comprises a plurality of muscles which cooperate with one another to cause contractions of the heart thereby to provide a pumping action. The heart requires blood flow to its muscles to provide its muscles with the necessary oxygen, nutrients, and the like, necessary for muscular contraction. It often happens that one or more of the blood vessels which feed the heart muscles becomes diseased and develops a blockage, or becomes occluded, or the like. When this happens, a region of the heart normally fed by that diseased blood vessel can experience a depletion, or interruption, of blood supply. If such a condition is not treated in a timely fashion, the patient may suffer a heart attack with often fatal results.

CABG procedures are often performed to circumvent such a blockage, or occlusion, in a diseased blood vessel, thereby to provide the region of the heart normally fed by the diseased vessel with blood. This procedure normally involves tapping blood from an appropriate blood source, such as a donor blood vessel such as, for example, the aorta, saphenous vein, mammary artery, or the like, and routing the tapped blood to the diseased vessel downstream of the occlusion or blockage. A variety of procedures are currently employed to provide tapped blood downstream of an occlusion, or blockage, in a diseased blood vessel. One procedure involves making use of a graft. In such a case, an end of the graft is typically sutured to an appropriate blood source to be in fluid flow communication therewith and an opposed end of the graft is typically sutured to a side of the diseased vessel to be in fluid flow communication therewith downstream of the occlusion, or blockage. Another procedure involves suturing a side of a healthy vessel to a side of a diseased vessel downstream of the blockage, or occlusion, so that blood can flow from the healthy vessel to the diseased vessel. A joint between an end of a vessel, or graft, and a side of another vessel, or graft, is often referred to as an end-to-side anastomosis. A joint between a side of a graft, or vessel, and a side of another graft, or vessel, is often referred to as a side-to-side anastomosis.

During CABG surgery, a patient is often connected to a cardiopulmonary bypass machine so that the heart can be stopped temporarily, thereby to ease the task of suturing the various grafts, and/or vessels, together. Furthermore, blood vessels, such as the aorta, for example, are often closed, or clamped, so as to interrupt blood flow through that vessel when that vessel is to be used as a donor vessel or blood source.

When CABG procedures are performed on a patient, the patient normally suffers a great deal of trauma. Accordingly, it would be beneficial if such CABG procedures could be improved so as to decrease patient trauma. In conventional CABG surgery, there are at least three factors that affect the degree of trauma suffered by a patient. These factors include: (1) the time the patient spends on a cardiopulmonary bypass machine, (2) the time the patient spends with a clamped blood vessel, such as the aorta, or the like, and (3) the quality of the anastomoses formed between the blood vessels and/or grafts. It is generally recognized that the risk of patient morbidity rises significantly after the patient has been placed on a cardiopulmonary bypass machine for a period of about one hour. Passage of blood through a cardiopulmonary bypass machine tends to damage blood cells consequently causing degradation in blood quality. Accordingly, the longer a patient is subjected to cardiopulmonary bypass, the more the blood cells become damaged and the higher the degradation in the quality of the blood. A complication often associated with prolonged placement on a cardiopulmonary bypass machine, is distal thrombosis. Distal thrombosis can give rise to embolization in the neurovasculature and can lead to the patient suffering a stroke. Accordingly, it would be beneficial if the period a patient spends on a cardiopulmonary bypass machine during CABG surgery could be reduced.

A factor by which the amount of time a patient spends on a cardiopulmonary bypass machine can be reduced is by reducing the time taken suturing the vessels and/or grafts together to form anastomoses. The average time taken to suture two vessels together to form an anastomosis in accordance with traditional suturing methods, is typically about seven to ten minutes. An average CABG procedure can involve the formation of about five anastomoses. Accordingly, the time spent on suturing during an average CABG procedure can be between about thirty-five to fifty minutes. Therefore, since the task of suturing can constitute a major portion of the one hour period, it would be advantageous if the time spent on such suturing could be reduced. By doing so, the time a patient is subjected to cardiopulmonary bypass would also be reduced, thereby reducing patient trauma and the risks of morbidity.

In so-called "off-pump" procedures, patients are not placed on cardiopulmonary bypass machines. Accordingly, the negative effects associated with cardiopulmonary bypass mentioned above are inhibited. However, the task of suturing is made more difficult since the task of suturing is normally then performed while the heart is beating. This can lead to the formation of anastomoses with reduced integrity. Improperly suturing blood vessels and/or grafts together may lead to post operative complications. Incorrect suturing during surgery requiring correction during the surgery, may unnecessarily extend the time taken to complete the surgery.

Suture placement devices have been proposed which enable a surgeon, or the like, to place suture elements in patient tissue without manually holding and manipulating a suture needle, as has traditionally been the case. Typically, this enables suture elements to be placed through vessels quicker than when traditional suturing techniques are used. It has been found that such suture placement devices can be rather cumbersome to operate. In particular, it has been found that approaching a vessel, during CABG surgery, for example, so as to position the device at an appropriate position at which the device can be actuated to place suture elements through the vessel, can be rather difficult. The device can have a plurality of needles, or the like, arranged selectively to advance and retract so as to pass the suture elements through the wall of the vessel. In addition, it can have actuating arrangements for selectively advancing and retracting the needles. Typically, the actuating arrangements and the needles, along with other parts of the device, are mounted on a common body.

It Would be advantageous to provide a suture placement device which is less cumbersome to operate and which is more easily manageable than the suture placement devices currently used. This should enable suturing operations to be conducted with greater accuracy and in a shorter period of time, especially during CABG surgery, whether use is made of an "off-pump" procedure or a cardiopulmonary bypass machine.

SUMMARY OF THE INVENTION

According to one aspect of the invention, there is provided a needle deployment device. The needle deployment device comprises a body, a plurality of medical needles displaceably mounted on the body and an actuator on the body, the actuator being actuatable in response to pressurizing a fluid so as to cause the needles to displace relative to the body.

It has been found that by providing such a needle deployment device where the actuator is actuatable in response to pressurizing a fluid, the device can be arranged to approach tissue and to be positioned relative to the tissue more easily than other needle deployment devices. One reason for this is that the device can be of a relatively compact design thereby enhancing its manageability and easing the task of positioning and holding it at an operative position relative to patient tissue, at which position the needles are to be deployed. When the device is used in an application to place suture elements through tissue, such as through a blood vessel wall during a CABG procedure, for example, the enhanced manageability of the device should enable sutures to be formed quicker and more accurately than other suture placement devices.

The actuator may comprise a piston displaceably mounted in a cylinder, the piston being displaceable relative to the cylinder in response to pressurizing the fluid. The needles may be operatively connected to the piston so that the needles displace relative to the body in response to the piston displacing relative to the cylinder. Accordingly, the device can then typically be actuated by pressurizing a fluid source at a remote location and in fluid flow communication with the device, so as to cause the piston of the device to ride in its associated cylinder thereby to deploy the needles.

According to another aspect of the invention, there is provided a medical system. The system comprises at least two bodies and a plurality of needles displaceably mounted on each body. The system further comprises an actuator on each body, each actuator being selectively actuatable in response to pressurizing a fluid so as to cause the needles to be displaced relative to their associated bodies.

According to another aspect of the invention, there is provided a method of performing a medical procedure. The method comprises pressurizing a fluid, actuating an actuator of a needle deployment device in response to pressurizing the fluid and causing a plurality of needles to displace in response to actuating the actuator.

In this way, the medical procedure can be performed by pressurizing a fluid source at a remote location and in fluid flow communication with the device, so as to cause the needles to be deployed by the device from the remote location.

BRIEF DESCRIPTION OF THE DRAWINGS

The invention will now be described, by way of example, with reference to the accompanying diagrammatic drawings, in which:

FIG. 1A shows a schematic side view of a patient's heart;

FIG. 1B shows a schematic cross-sectional side view of an end-to-side anastomosis between two vessels;

FIG. 1C shows a schematic cross-sectional side view of a side-to-side anastomosis between two vessels;

FIG. 2A shows a schematic side view of a suture placement system incorporating a needle deployment system in accordance with the invention, the suture placement system comprising two suture placement devices each incorporating a needle deployment device in accordance with the invention, the system being arranged to form a side-to-side anastomosis;

FIG. 2B shows a schematic cross-sectional view of a flexible member of the system shown in FIG. 2A along arrows II—II in FIG. 2A;

FIG. 3 shows, at an enlarged scale, a schematic three-dimensional view of part of one of the needle deployment devices, or suture placement devices, of the system shown in FIG. 2A;

FIG. 4 shows a schematic three-dimensional exploded view corresponding to FIG. 3;

FIG. 5 shows a schematic three-dimensional view of part of a suture holder of the suture placement device shown in FIG. 3;

FIG. 6 shows a schematic three-dimensional view of a suture support of the suture placement device shown in FIGS. 3;

FIG. 7A shows, at an enlarged scale, a schematic three-dimensional view of part of the suture support shown in FIG. 6;

FIG. 7B shows a schematic three-dimensional view of an end of a suture element secured to a cuff;

FIG. 7C shows a schematic side view of part of the suture support of FIG. 7A indicating how the cuff of FIG. 7B is received in a seat defined by the part of the suture support shown in FIG. 7A;

FIGS. 8A to 8E show schematic side views of one of the suture placement devices in accordance with the invention and illustrates sequential steps indicating the operation of the suture placement device;

FIG. 9 shows a schematic three-dimensional view of the suture support of one of the devices of the system shown in FIG. 2A, the support being operatively positioned to extend through an aperture in a side of a blood vessel;

FIG. 10 shows a schematic three-dimensional view corresponding to FIG. 9, and shows engaging elements of the suture placement device after the engaging elements have engaged ends of a plurality of suture elements and have drawn the ends through a wall of the vessel adjacent the aperture to place the sutures in the vessel wall;

FIG. 11 shows a schematic end view along arrow III in FIG. 10 and shows the suture support being removed from the vessel through the aperture after the suture elements have been placed in the vessel wall adjacent the aperture;

FIG. 12 shows a schematic three-dimensional view corresponding to FIGS. 9 and 10, and shows the suture support having been withdrawn from the vessel through the aperture after the suture elements have been placed in the vessel wall;

FIG. 13 shows a schematic view of one of the suture placement devices being supported at a position remote from a vessel on which a plurality of suture elements have been placed using the device;

FIG. 14 shows a schematic three-dimensional view of the suture holders of both suture placement devices of the system shown in FIG. 2A, after the one device has been used to place suture elements in a wall of a target vessel adjacent an aperture in the target vessel and the other device has been used to place the suture elements through a wall of a donor vessel adjacent an aperture in the donor vessel;

FIG. 15 shows a three-dimensional schematic view corresponding to FIG. 14, one part of the suture holder of the one device having been paired with one part of the suture holder of the other device thereby to bring opposed end portions of the same suture elements together;

FIG. 16 shows a schematic three-dimensional view showing a suture-handling device being passed across paired end portions of the suture elements after the opposed end portions have been paired up;

FIG. 17 shows a schematic three-dimensional view corresponding to FIG. 16, the suture-handling device having been passed across the paired end portions of the same suture elements, each pair of opposed portions of the suture element having been received in a slot of the suture-handling device;

FIG. 18 shows a schematic three-dimensional view corresponding to FIG. 17 and shows the vessel walls of the target and donor vessels having been drawn together and the suture elements having been pulled through the vessel walls;

FIG. 19 shows a schematic side view of another suture placement system which incorporates the needle deployment system in accordance with the invention, the suture placement system comprising two suture placement devices each comprising a needle deployment device in accordance with the invention, the suture placement system being arranged to form an end-to-side anastomosis;

FIG. 20 shows a schematic three-dimensional view of one of the suture placement devices of the system shown in FIG. 19, the device being arranged to place suture elements through a vessel wall at an end of a vessel adjacent a mouth of the vessel;

FIG. 21 shows, at an enlarged scale, part of the device shown in FIG. 20, a suture holder retainer of the suture placement device being shown in an open condition;

FIG. 22 shows, at an enlarged scale, a schematic part sectional side view of part of a vessel support shaft of the suture placement device, a needle of the suture placement device being shown in a dormant position within a passage defined in the shaft;

FIG. 23 shows a schematic part sectional side view corresponding to FIG. 22, the needle of the suture placement device having been displaced from its dormant position to an extended position;

FIG. 24 shows a schematic three-dimensional view corresponding to FIG. 20, a suture holder retainer of the suture placement device being shown in an open condition and further showing a plurality of suture elements, end portions of which are attached to ends of needles;

FIG. 25 shows a schematic three-dimensional view corresponding to FIG. 24, and shows an end portion of a vessel or graft received on the vessel support shaft of the suture placement device;

FIG. 26 shows a schematic three-dimensional view corresponding to FIG. 25 and shows the suture holder retainer in a closed condition after the end portion of the vessel or graft has been positioned on the vessel support shaft;

FIG. 27 shows a schematic three-dimensional view corresponding to FIG. 26, the suture holder retainer being shown in an open condition and further showing the needles having been passed through the vessel or graft adjacent a mouth of the vessel or graft supported on the vessel support shaft;

FIG. 28 shows a schematic three-dimensional view of the end portion of the graft, after the needles of the suture placement device have been passed through the graft adjacent its mouth, the needles being held on suture holders of the suture placement device, the suture holders having been removed from the suture holder retainers of the suture placement device;

FIG. 28A shows a schematic three-dimensional view of one of the suture holders normally retained on an associated suture holder retainer of the device, the suture holder being shown having a shape corresponding to its shape when retained on its associated suture holder retainer; and FIG. 28B shows a schematic three-dimensional view of the suture holder of FIG. 28A having a shape corresponding to its shape when in a relaxed condition after having been removed from its associated suture holder retainer.

DESCRIPTION OF THE SPECIFIC EMBODIMENTS

Referring to FIG. 1A of the drawings, a patient's heart is generally indicated by reference numeral 10. The heart 10 is shown after a CABG procedure has been performed thereon. The CABG procedure involved suturing an end 12.1 of a graft 12 to the aorta 14 and an opposed end 12.2 of the graft 12 to a target vessel 16 downstream of a blockage, or occlusion 18, in the target vessel 16. After completion of the CABG procedure, blood is supplied to a region of the heart downstream of the occlusion 18, which region was subjected to a depletion, or starvation, of blood, because of the occlusion 18 in the vessel 16.

During the CABG procedure, an incision was made in the aorta 14 and the vessel 16 respectively. The graft 12 was sutured to the aorta 14 and the vessel 16 such that open mouths at the ends 12.1, 12.2 of the graft 12 are connected to the aorta 14 and vessel 16 respectively so that blood can flow through the incision in the aorta 14, through the mouth of the graft 12 at its end 12.1, internally along the graft 12, through its mouth at its end 12.2 and through the incision in the target vessel 16, and then along the vessel 16 downstream of the occlusion 18. In this way, blood is tapped from the aorta 14 and supplied to the region of the heart normally supplied by the vessel 16, if not for the occlusion 18. When the ends 12.1, 12.2 were joined to the aorta 14 and vessel 16 respectively, anastomoses were thus formed at 22, 24 respectively. The graft 12 was joined to the aorta 14 and vessel 16 by means of sutures 26 to form the anastomoses 22, 24.

The anastomoses at 22, 24 are examples of what is often termed end-to-side anastomoses. The end-to-side anastomosis at 22 is shown schematically, and in greater detail, in FIG. 1B of the drawings, in which like reference numerals have been used to designate similar parts or features, unless otherwise stated. A CABG procedure can involve forming one or more side-to-side anastomoses. An example of such a side-to-side anastomosis is indicated generally by reference numeral 20 in FIG. 1C of the drawings. The side-to-side anastomosis 20 extends between a side 21.1 of a vessel 21 and an opposed side 23.1 of another vessel 23. By means of such a side-to-side anastomosis 20, blood can flow from one of the vessels 21, 23 to the other of the vessels 21, 23. In this way, blood can be tapped from one of the vessels 21, 23 to the other of the vessels 21, 23 at a position downstream of a blockage, or occlusion, in the other of the vessels 21, 23.

A needle deployment system, in accordance with the invention, incorporated in a suture placement system, which can be used advantageously to form a side-to-side anastomosis as indicated in FIG. 1C, will now be described with reference to FIGS. 2A and 2B of the drawings.

Referring to FIG. 2A, the suture placement system for forming a side-to-side anastomosis is generally indicated by reference numeral 110. The system 110 includes two needle deployment devices, in accordance with the invention, which are incorporated in two suture placement devices generally indicated by reference numerals 112, 114 respectively. Each device 112, 114 is an example of a needle deployment device in accordance with the invention.

Each device 112, 114 comprises a body 115 and a suture holder, generally indicated by reference numeral 116. In the embodiment of the invention shown in FIG. 2A, each holder 116 comprises two parts 116.1, 116.2. Each of the bodies 115 further comprises a suture support, generally indicated by reference numeral 118.

The devices 112, 114 are connected together by an elongate flexible member 120. The member 120 can be formed of any appropriate flexible material, such as a synthetic plastics material, or the like. The material of which the member 120 is made is preferably bio-compatible. The member 120 defines two conduit portions 121.1, 121.2 extending longitudinally in series along one side 122 of the member 120. The member 120 further defines a suture container portion 121.3 for containing portions of a plurality of suture elements extending between the devices 112, 114, as will be described in greater detail below. The suture container portion 121.3 extends longitudinally along an opposed side 124 of the member 120. The member 120 further defines a longitudinally extending web 126 that connects the two conduit portions 121.1, 121.2 on the side 122 of the member 120 to the suture container portion 121.3 on the opposed side 124 of the member 120.

The system 110 comprises another elongate flexible member generally indicated at 130. The member 130 can typically be formed of a material which is the same as the material of which the member 120 is made. Accordingly, it can be formed from a synthetic plastics material and is preferably bio-compatible. The member 130 defines two conduit portions 131.1, 131.2 extending longitudinally along opposed sides 132, 134 thereof. The conduit portions 131.1, 131.2 are connected together by means of a longitudinally extending web 136 extending along and between the conduit portions 131.1, 131.2 for a portion of their lengths. The web 136 connecting the conduit portions 131.1, 131.2 together ends at 138. From the end of the web 136 at 138, the conduit portions 131.1, 131.2 are free of each other. Each conduit portion 131.1, 131.2 carries a female Luer-type connector 140 at a free end 142 thereof. The female Luer-type connectors 140, 140 are arranged to be releasably connectable to complementary male Luer-type connectors on syringes (not shown).

The member 130 is connected to the member 120 at 143 such that ends 144, 144 of the conduit portions 131.1, 131.2 are connected to the conduit portions 121.1, 121.2 respectively, to be in fluid flow communication therewith. To this end, the ends 144, 144 are provided with laterally outwardly protruding formations 128 which extend into the conduit portions 121.1, 121.2 respectively. Advantageously, the formations 128, 128 are received in the conduit portions 121.1, 121.2 to permit angular displacement of the member 130 relative to the member 120 as indicated by arrows A. A fluid flow passage indicated in dashed lines by reference numeral 146 extends from one of the female Luer-type connectors 140, along the conduit portions 131.1, 121.1, to the device 112. Another fluid flow passage indicated in dashed lines by reference numeral 148 extends from the other of the female Luer-type connector 140, along the conduit portions 131.2, 121.2, to the device 114.

The body 115 of each device 112, 114 includes a cylinder 150 defining an internal chamber 152. The conduit portions 121.1, 121.2 are connected in fluid flow communication with the internal chambers 152, 152 through ports 153, 153. A piston 155 is received in the cylinders 150, 150 of each device 112, 114. The body 115 of each device 112, 114 comprises a shaft 154 on which its associated piston is mounted. The shafts 154, 154 are selectively extendable and retractable relative to the cylinders 150, 150 as indicated by arrows B, in response to pressurizing and de-pressurizing the chambers 152, 152. Pressure relief valves 151, 151 are provided in the conduit portions 131.1, 131.2 so as to inhibit the chambers 152, 152 from being pressurized beyond a predetermined pressure, as will be described in greater detail herein below.

The system 110 further comprises a plurality of suture elements. In FIG. 2A, one of the suture elements is indicated schematically in dashed lines by reference numeral 160. Each of the suture elements defines opposed ends at 160.1, 160.2 respectively. The end 160.1 of each of the suture elements 160 is supported on the suture support 118 of the device 112 and the opposed end 160.2 of each suture element 160 is supported on the suture support 118 of the other device 114. The suture elements 160 extend from the suture support 118 of the device 112, snugly adjacent an outer surface of the cylinder 150 of the device 112 and into a lumen 121.4 defined within the suture container portion 121.3 of the member 120. The suture elements then extend longitudinally along the lumen 121.4, out from the lumen 121.4 at the device 114, and then snugly adjacent an outer surface of the cylinder 150 of the other device 114 to the support 118 of the other device 114.

As can best be seen with reference to FIG. 2B of the drawings, in which like reference numerals have been used to designate similar parts and features unless otherwise stated, the portion 121.3 defines a longitudinally extending slit 121.5 through which the suture elements 160 can be drawn from the longitudinally extending lumen 121.4. The portion 121.3 defines opposed longitudinally extending flange portions 121.6, 121.7 between which the slit 121.5 is defined. Longitudinally extending free edges of the flange portions 121.6, 121.7 are resiliently urged toward each other thereby resiliently to keep the slit 121.5 in a closed condition so as to contain, or hold, the portions of the suture elements extending along the lumen 121.4 within the lumen 121.4. When the suture elements 160 are drawn from the portion 121.3, the free edges of the flange portions 121.6, 121.7 part readily to permit the suture elements to be drawn from the lumen 121.4 with little effort.

Referring now to FIGS. 3 to 7 of the drawings, certain parts of the devices 112, 114 will now be described in greater detail. The suture support 118 of each device 112, 114 comprises a foot portion 118.1 and a shaft portion 118.2. The foot portion 118.1 is attached to an end of the shaft portion 118.2. As can best be seen in FIG. 6, an opposed end of the shaft portion 118.2 has a hole 118.3 extending therethrough. The suture support 118 is secured relative to the cylinder 150 by means of a connecting pin (not shown) extending through the hole 118.3. The connecting pin is typically secured on the body 115. As can best be seen in FIG. 4 of the drawings, the shaft 154 has a longitudinally extending slot 154.1. When the shaft 154 is selectively extended and retracted relative to its associated cylinder 150 in response to pressurizing and de-pressurizing the associated chamber 152, the connecting pin securing the suture holder 118 on the body 115 rides in the slot 154.1 so as not to interfere with displacement of the shaft 154.

As mentioned, the suture holder 116 of each device 112, 114 has two parts 116.1, 116.2. Each part 116.1, 116.2 is releasably held on the shaft of its associated body 115. To this end, each part 116.1, 116.2 has a catch formation 116.3 for resiliently engaging in a complementary slot, or recess, 154.2 on the shaft 154. As can best be seen in FIG. 3 of the drawings, the parts 116.1, 116.2 are disengagable from the shaft 154 by causing them to bend resiliently so that the catch formations 116.3, 116.3 disengage from the recesses 154.2, as indicated by arrows C. The parts 116.1, 116.2 of the suture holders 116 can be formed from any appropriate material such as a resilient synthetic plastics material, or the like. Preferably, the parts 116.1, 116.2 are of a biocompatible material. Typically, when the catch formations 116.3, 116.3 are caused to disengage from the shaft 154, the parts 116.1, 116.2 bend resiliently in the regions indicated at 116.5.

Conveniently, the parts 116.1, 116.2 have laterally outwardly protruding portions, generally indicated by reference numerals 116.6, 116.6, to enable the parts to be manipulated between a thumb and index finger, for example, of a user's hand. The parts 116.1, 116.2 further comprise inclined surfaces 116.4, 116.4. The surfaces 116.4, 116.4 are arranged to cooperate with the body 115 so that when the shaft 154 is retracted into its associated cylinder 150 by an amount exceeding a predetermined amount, the inclined surfaces 116.4 ride against the body 115 so as to urge the catch formations 116.3 from the recesses 154.2 thereby to cause the parts 116.1, 116.2 to disengage from the shaft 154 automatically, as will be described in greater detail herein below.

The parts 116.1, 116.2 of the suture support 116 further comprise a plurality of engaging elements for engaging the ends 160.1, 160.2 of the suture elements 160 on the suture supports 118, 118. The engaging elements can be of any appropriate form so as to cooperate with the ends 160.1, 160.2 of the suture elements 160 so as to enable the ends 160.1, 160.2 of the suture elements 160 to be engaged by the engaging elements. Conveniently, the engaging elements are in the form of needles 170 and are arranged to engage cuffs to which the ends of the suture elements are secured, as will be described in greater detail below. It will be appreciated that any appropriate engaging arrangement between the suture element ends and the engaging elements can be used instead of needles and cuffs. For example, use can be made of hook and loop arrangements, lasso-like arrangements, or the like.

As can best be seen in FIGS. 4 and 5 of the drawings, the needles 170 are secured in holes, or apertures, 172 extending through the parts 116.1, 116.2. The needles 170 are arranged to engage with the ends 160.1, 160.2 of the suture elements 160 held on the suture supports 118, 118. As can best be seen with reference to FIGS. 7A to 7C of the drawings, the foot portion 118.1 of the suture holder 118 comprises a plurality of seats 118.4. Each seat 118.4 defines a cross-sectionally part circular hole 118.5 defining a laterally extending slit 118.7. A circumferentially intruding collar formation 118.6 is provided at the base of each hole 118.5. As can best be seen with reference to FIG. 7B, the end 160.1, 160.2 of each suture element 160 is secured to a cuff 117 whereby the end of the suture element is held on the support 118. Each cuff 117 comprises a cylindrical member 117.1 having an axially extending hole 117.2. Conveniently, the end 160.1, 160.2 of each suture element 160 is secured to an associated cuff 117 by inserting the end into the hole 117.2 at one end of the cuff 117 and securing the end 160.1, 160.2 of the suture element 160 to the cuff 117. Naturally, the end of the suture element 160 can be secured to the cuff 117 in any appropriate manner, such as, by using an appropriate adhesive, by means of soldering or welding, by means of an interference fit, by means of crimping, or the like. Instead, the cuffs can be formed integrally on the ends of the suture elements 160.

The ends 160.1, 160.2 of the suture elements 160 are releasably held on the foot 118.1 of the suture support 118 by means of the cuffs 117 being seated in the seats 118.4. When the needles 170 of the holders 116 are advanced relative to the body 115 in response to the shaft 154 being extended, the needles follow paths that are in register with the holes 117.2 in the cuffs 117 when the cuffs are seated in the seats 118.4. The needles 170 have pointed ends 170.1 arranged to pass into the holes 117.2 so as to engage with the cuffs 117. The lateral dimensions of the needles 170 at their pointed ends 170.1 and an internal diameter of the holes 117.2 are arranged to cooperate such that when the ends 170.1 of the needles 170 are advanced into the holes 117.2, the cuffs 117 are deformed radially outwardly so as to be frictionally engaged on the pointed ends 170.1 of the needles 170. After such engagement, the needles 170 can be withdrawn from the foot portion 118.1 in sympathy with retraction of the shaft 154 in response to retraction of the piston 155 in the cylinder 150. As the needles 170 are withdrawn in this fashion, the cuffs 117, and consequently also the ends 160.1, 160.2 of the suture elements 160 secured to the cuffs 117, are withdrawn from the seats 118.4.

Referring now to FIGS. 8A to 8E of the drawings, the operation of one of the devices 112, 114 will now be described in greater detail. In FIGS. 8A to 8E, the same reference numerals have been used to designate similar parts and features unless otherwise stated. For the sake of convenience, operation of the device 112 will be described.

It will be appreciated that the device 114 operates in a manner similar to that of the operation of the device 112.

To operate the device 112, a syringe (not shown) is operatively connected to the female Luer-type connector 140 connected in fluid flow communication with the internal chamber 152 of the device 112, as can best be seen with reference to FIG. 2A. A plunger of the syringe is then depressed to cause an appropriate fluid, such as air, a saline solution, or the like, to flow along the fluid flow passage 146 in fluid flow communication with the chamber 152 of the device 112. In this way, the chamber 152 is pressurized so as to cause the piston 155 to advance within the cylinder 150, as indicated by arrow D in FIG. 8A. In consequence, the shaft 154 is caused to advance in sympathy with advancement of the piston 155. Since the suture holder 116 is engaged on the shaft 154, it is caused to advance also. As the suture holder 116 advances, the needles 170 of the parts 116.1, 116.2 of the holder 116, advance toward the cuffs 117 on the foot 118.1 of the suture support 118. Eventually, as can best be seen in FIG. 8B, the pointed ends 170.1 of the needles 170 are urged into the holes 117.2 of the cuffs 117 so as to cause the cuffs to be engaged on the ends 170.1 of the needles 170. Accordingly, since the ends 160.1 of the suture elements 160 are secured to the cuffs 117, the ends 160.1 are then also engaged with the needles 170.

With reference to FIG. 2A, the relief valve 151 operatively connected in the fluid flow passage 146 is provided to inhibit the needles 170 from being advanced too far. The pressure relief valve 151 is typically arranged so as to relieve pressure in the fluid flow passages 146 at a pre-determined pressure corresponding to when the needles 170 have engaged with the cuffs 117. It will be appreciated that resistance to advancement of the needles 170 into the holes 117.2 of the cuffs 117 increases after the cuffs 117 have been engaged. In consequence, when the cuffs 117 have been engaged, an increase in pressure is required in the chamber 152 to cause the needles 170 to advance further. By providing the pressure relief valve 151 in the fluid flow passage 146 so as to relieve pressure when the pressure increases beyond the pressure needed to cause the needles 170 to engage the cuffs, over extension of the needles 170 is inhibited. When the predetermined pressure in the fluid flow passage 146 is reached, the fluid in the fluid flow passage expels from the passage 146 through the valve 151. The valve 151 is conveniently placed so that the expulsion of the fluid from the passage 146 is readily detectable by a user of the system 110, thereby to serve as a signal to the user that the cuffs 117 have been engaged and that depression of the plunger of the syringe can now stop.

In FIG. 8B, the needles 170 are shown in a condition in which the cuffs 117 on the foot portion 118.1 have been engaged. The plunger of the syringe can then be withdrawn into its cylinder thereby to cause the chamber 152 of the device 112 to depressurize so as to cause the piston 155 to retract into the cylinder 150. As the piston 155 retracts in this fashion, the needles 170 are withdrawn from the foot portion 118.1 of the suture holder 118. As can best be seen with reference to FIG. 8C, as the needles 170 withdraw, the ends 160.1 of the suture elements 160, now engaged on the needles 170 by means of the cuffs 117, are withdrawn from the foot 118.1.

As can further be seen with reference to FIG. 8C, as the shaft 154 is caused to retract further, a stage is reached when the inclined surfaces 116.4, 116.4 of the parts 116.1, 116.2 of the holder 116 make contact with the body 115 of the device 112. The part of the body 115 with which the inclined surfaces 116.4 make contact, is indicated by reference numeral 115.1 in FIGS. 8A to 8E. As the shaft 154 is caused to retract further, the inclined surfaces 116.4 ride along an outer peripheral edge of the part 115.1. In consequence, the portion 116.6 of each part 116.1, 116.2 of the holder 116 are urged laterally away from the body 115 thereby causing the portions 116.5 to bend resiliently and the catch formations 116.3, 116.3 to disengage from the recesses 154.2 on the shaft 154. In this manner, the parts 116.1, 116.2 become disengaged from the shaft 154 and therefore also from the body 115 of the device 112, as can best be seen in FIG. 8D.

As can best be seen with reference to FIGS. 4 and 5 of the drawings, the parts 116.1, 116.2 of the holder 116 have channel formations 116.7. The channel formations 116.7 together define a passage through which the shaft portion 118.2 of the suture support 118 extends when the parts 116.1, 116.2 are mounted on the body 115 of the device 112. The channel formations 116.7 are arranged to embrace the shaft 118.2 so that when the catch formations 116.3, 116.3 of the parts 116.1, 116.2 are disengaged from the shaft 154 of the body 115 of the device 112, the parts 116.1, 116.2 are frictionally held on the shaft 118.2 by virtue of the shaft 118.2 being embraced by the parts 116.1, 116.2 in the channels 116.7, 116.7. Accordingly, as shown in FIG. 8D, the parts 116.1, 116.2 are retained on the shaft portion 118.2 after the catch formations 116.3 have disengaged from the recesses 154.2 of the shaft 154.

As can best be seen in FIG. 8E, after disengagement of the parts 116.1, 116.2 from the shaft 154, the portions 116.6, 116.6 of each part 116.1, 116.2 of the holder 116 can then be gripped between a thumb and finger of a user, for example, so that the parts 116.1, 116.2 can be removed manually from the body 115 of the device 112, as indicated by arrows G.

The system 110 will now be described in use and with reference to FIGS. 9 to 18 of the drawings. The system 110 will be described, by way of example, with reference to forming a side-to-side anastomosis between two blood vessels during a CABG procedure.

Referring initially to FIG. 9 of the drawings, to form such a side-to-side anastomosis between two vessels, an incision, or cut, 180 is made in a target vessel 182. Typically, the target vessel 182 can have an occlusion, or the like, upstream of the incision 180, which occlusion interrupts, or reduces, blood flow to a region of the heart downstream of the occlusion. To form a side-to side anastomosis, a spacing pattern of the ends 116.1 on the support 118 of the device 112, generally indicated by reference numeral 184 in FIG. 9A of the drawings, is generally the same for both devices 112, 114. The spacing pattern 184 of the ends 116.1 of the suture elements on the foot portion 118.1 of the device 112 can best be seen with reference to FIG. 9A of the drawings. Accordingly, the devices 112, 114 can typically be used interchangeably to place suture in either the target vessel 182 or a donor vessel, from which blood is to be tapped to the target vessel, as will be described in greater detail herein below. In the discussion which follows, by way of example, the device 112 will be used to place suture in the target vessel 182 and the device 114 will be used to place suture in the donor vessel.

The incision 180 should preferably be of a length which corresponds to the spacing pattern 184 of the suture ends on the foot portion 118.1, so that when a side-to-side anastomosis has been formed between the vessels by the system 110, the anastomosis will have a high degree of integrity. It will be appreciated that, should the incision 180 be formed to have too great a length, leakage of blood could ensue after the anastomosis has been formed. Should the incision 180 have too short a length, blood flow through the anastomosis can be impeded unnecessarily. Therefore, it would be advantageous if the incision 180 could be formed to have a specific predetermined length, which corresponds to the spacing pattern of the suture ends 116.1 on the support 118 of the device 112. It would further be advantageous if such an incision 180 could be formed accurately, repeatedly, and with little effort. To form the incision 180 such that it has a length which corresponds to the spacing pattern of the suture ends 116.1 on the support 118, use can be made of a surgical scissors arranged to form a cut, or aperture, of predetermined length. Such a scissors is disclosed in Applicant's co-pending patent application Ser. No. 09/610,564, filed Jun. 30, 2000, entitled "Scissors", the full disclosure of which is incorporated herein by reference.

After the incision 180 has been made in the target vessel 182, the suture support 118 of the device 112 is passed through the incision 180 such that the foot portion 118.1 is positioned within a lumen 182.2 defined by the vessel 182. The foot portion 118.1 has a shape so as to enable it to be inserted through the incision 180 relatively easily, while inhibiting damage to a vessel wall 182.1 of the vessel 182 immediately adjacent the incision 180. To this end, and as can best be seen in FIG. 9A of the drawings, the foot portion 118.1 has a leading end portion 118.8 and a heel portion 118.9. The foot portion 118.1 is inserted through the incision 180 and into the lumen 182.2 in a manner similar to when a person inserts his or her foot into a shoe. Accordingly, the leading end portion 118.8 of the foot portion 118.1 is passed through the incision 180 first and at an inclined orientation relative to the vessel wall 182.1. Conveniently, the foot portion 118.1 defines tapering forward and rearward ends having rounded corners to ease the task of passing the foot portion 118.1 through the incision 180. As the leading end portion is passed through the incision 180, the foot portion 118.1 is urged in a forward direction and tilted so as to pass the heel portion 118.9 through the incision 180. The foot portion 118.1 is then urged in a rearward direction until the shaft portion 118.2 seats snugly against an operatively rear end 180.1 of the incision 180. The foot portion 118.1 is then lifted to lie against an interior surface 182.3 of the wall 182.1 adjacent the incision 180, so that the ends 160.1 of the suture elements 160 secured on the cuffs 117 lie immediately adjacent the interior surface 182.3. In this position, the cuffs 117 to which the ends 160.1 of the suture elements 160 are secured, are positioned such that peripheral portions of the vessel wall 182.2 immediately adjacent the incision 180 lie snugly over the cuffs 117. The foot portion is then in an operative position at which it is positioned relative to the vessel wall such that when the device 112 is actuated, the suture elements will be correctly placed through the vessel wall relative to the incision 180.

After the foot portion 118.1 has been so positioned, and as can best be seen with reference to FIG. 10 of the drawings, the device 112 is actuated to place the suture elements 160 in the vessel wall 182.2 adjacent the incision 180. As mentioned above, this is achieved by actuating the syringe connected in fluid flow communication with the chamber 152 of the device 112. In this manner the needles 170 of the parts 116.1, 116.2 of the suture holder 116 are advanced toward the foot portion 118.1. As the needles 170 are advanced, they pierce and pass through the vessel wall 182.1 adjacent the incision 180 and then engage the cuffs 117 on the foot portion 118.1. After the cuffs 117 have been engaged, and as the user depresses the plunger of the syringe further, fluid is caused to expel from the relief valve 151, as described above, indicating to the user that the cuffs have been engaged. The plunger of the syringe is then withdrawn to cause the needles 170 to withdraw from the foot portion 118.1 while the cuffs 117 are engaged on the ends 170.1 of the needles 170 thereby to pass the ends 160.1 of the suture elements through the vessel wall adjacent the incision 180. The plunger of the syringe is typically withdrawn until the parts 116.1, 116.2 are disengaged from the shaft 154 so that they are held frictionally on the shaft portion 118.2 as shown in FIG. 8E and as described above.

After the ends 160.1 of the suture elements 160 have been passed through the vessel wall 182.1 in this fashion, the foot portion 118.1 is removed from the target vessel 182 through the incision 180. To do this, and as can best be understood with reference to FIGS. 7A to 7C and FIG. 11 of the drawings, the suture elements 160 are displaced laterally from the seats 118.4 of the foot portion 118.1 and through the slits 118.7, so as to be free of the foot portion 118.1. Typically, the suture elements 160 extend from the seats 118.4 operatively below the foot portion 118.1 and up along a side of the shaft portion 118.2 which is positioned adjacent the heel portion 118.9 of the foot portion 118.1. The suture elements are typically made from a material having a degree of resilience. Accordingly, the suture elements typically flex in a lateral direction so as to pass naturally from the seats 118.4 through the slits 118.7 when the cuffs 117 are withdrawn from the seats 118.4. Instead, or in addition, and as can best be seen in FIG. 11 of the drawings, the suture elements can be caused to pass through the slits 118.7 by gently rocking the foot portion 118.1 in a sideways direction as indicated by arrows H—H. When the foot portion 118.1 is rocked gently in this fashion, the suture elements 160 can be passed through the slits 118.7 so as to be free of the foot portion 118.1. After the suture elements have been freed from the foot portion 118.1, the foot portion 118.1 is removed from the vessel 182 through the incision 180, as can best be seen in FIG. 12 of the drawings. The parts 116.1, 116.2 of the suture holder 116 can be removed from the shaft 154 of the device prior to removing the foot portion 118.1 from the vessel 182.

Referring to FIG. 13, after the suture elements 160 have been placed through the target vessel 182 as described above, the device 112 can be removed from a surgical site 190, at which the anastomosis is to be formed, and held at a convenient location 192 remote from the surgical site 190 until the opposed ends 160.2 of the suture elements 160 supported on the suture support 118 of the device 114 have been placed through the donor vessel, as described in greater detail herein below. Conveniently, the device 112 can be held on an appropriate bracket, clamp, support, or the like, remote from the surgical site 190 and while the parts 116.1, 116.2 of its suture holder 116 are held thereon. In the case where a sternotomy 193 has been performed, for example, to provide access to the heart for performing the CABG procedure, the device 112 can be held on a support, or the like, mounted on a bracket 194 holding the sternotomy 193 in an open condition. An appropriate support for holding the device 112 at a position 192 remote from the surgical site 190, is disclosed in Applicant's co-pending patent application Ser. No. 09/608,832, filed on Jun. 6, 2000, entitled "Support Clamp", the full disclosure of which is herein incorporated by reference.

As the device 112 is removed from the surgical site 190 after placement of the suture elements through the target vessel, portions of the suture elements 160 contained in the suture container portion 121.3 of the elongate flexible member 120 and adjacent the device 112 are drawn from the lumen 121.4 through the slit 121.5, as can best be understood with reference to FIGS. 2A and 13 of the drawings.

Referring to FIG. 14, after the ends 160.1 of the suture elements 160 have been placed through the target vessel 182, and the device 112 has been positioned remote from the surgical site as described above, the opposed ends 116.2 of the suture elements 160 are placed through the donor vessel. The donor vessel is generally indicated by reference numeral 196 in FIG. 14. The ends 160.2 are placed through the donor vessel 196 in a fashion similar to that described above, but using the device 114. After the device 114 has been used to place the opposed ends 160.2 of the suture elements 160 through the donor vessel 196, it is removed from the surgical site 190. As it is removed, and as can best be understood with reference to FIGS. 2A and 13 of the drawings, portions of the suture elements 160 contained in the suture container portion 121.3 of the elongate flexible member 120 and adjacent the device 114 are drawn from the lumen 121.4 and through the slit 121.5. By having retained the portions of the suture elements 160 in the suture container portion 121.3 of the elongate flexible member 120 in this fashion, the portions were inhibited from becoming entangled during the placement of the suture elements in the target and donor vessels respectively. After the device 114 has been used to pass the opposed ends 160.2 of the suture elements 160 through the donor vessel 196, it too can be supported at a convenient location remote from the surgical site 190, in a fashion similar to that described above with reference to the device 112. Instead, the device 114 can be held in a user's hand, or otherwise positioned, remote from the surgical site 190.

In FIG. 14, only the parts 116.1, 116.2 of the suture holders 116, 116 of the respective devices 112, 114 are shown for the sake of clarity and after the opposed ends 116.2 of the suture elements 160 have been passed through the donor vessel 196 by the device 114. Typically, immediately after the suture elements 160 have been placed through the target and the donor vessels respectively, the suture holder 116 of each device 112, 114 is held on the shaft portions 118.2, 118.2 of their associated suture holders 118, 118 as described above.

The parts 116.1, 116.2 of the suture holder 116 of each device 112, 114 are then removed from the shaft portions 118.2, 118.2. It will be appreciated that each of the suture elements 160 extends between one of the parts 116.1, 116.2 of the suture holder 116 of the device 112 and one of the parts 116.1, 116.2 of the suture holder 116 of the device 114. As indicated in the drawings, five suture elements 160 extend between the part 116.1 of the suture holder 116 of the device 112 and the part 116.1 of the suture holder 116 of the device 114. Furthermore, five suture elements 160 extend between the part 116.2 of the suture holder 116 of the device 112 and the part 116.2 of the suture holder 116 of the device 114. In the present application, namely to form a side-to-side anastomosis during a CABG procedure, it has been found that a total of ten suture elements 160 is sufficient to form a typical side-to-side anastomosis. However, it will be appreciated that the system 110 can be provided with any appropriate number of suture elements depending on the intended application for which the system is to be used.

After the parts 116.1, 116.2 of the holders 116, 116 of the devices 112, 114 have been removed from the bodies 115, 115 of the devices 112, 114, the part 116.1 of the holder 116 of the device 112 is paired with the part 116.1 of the holder 116 of the device 114, so that the opposed ends 160.1, 160.2 of the five suture elements extending between the parts 116.1, 116.1 are paired up with each other. FIG. 15 shows the part 116.1 of the suture holder 116 of the device 112 paired with the part 116.1 of the suture holder 116 of the other device 114. In this fashion, the opposed ends of the same suture elements are paired with each other. In FIG. 15, each of the five suture elements extending between the parts 116.1, 116.1 are indicated by reference numerals 160A, 160B, 160C, 160D and 160E. The opposed ends of the suture elements are indicated by reference numerals 160.1A and 160.2A, 160.1B and 160.2B, 160.1C and 160.2C, 160.1D and 160.2D, and, 160.1E and 160.2E. The parts 116.2, 116.2 are not shown in FIG. 15 for the sake of clarity.

Conveniently, the parts 116.1, 116.2 of the suture holders 116, 116 can bear an appropriate form of identification to ease the task of determining which of the parts 116.1, 116.2 of the device 112 carries the opposed ends of the suture elements carried on which of the parts 116.1, 116.2 of the device 114. For example, the parts 116.1, 116.2 of the holders 116, 116 can be distinctively colored to enable a user to determine readily which part 116.1, 116.2 belongs with which other part 116.1, 116.2. For instance, presuming the part 116.1 of the device 112 carries an end of each of five of the suture elements and the part 116.1 of the device 114 carries the opposed ends of the same five suture elements, then the parts 116.1, 116.1 can typically be of the same color, such as black, for example. The other part 116.2 of the device 112 then carries an end of each of the five other suture elements and the part 116.2 of the device 114 then carries the opposed ends of the same five other suture elements. The parts 116.2, 116.2 can then be of the same color but a color different to the color of the parts 116.1, 116.1. For example, they can be colored white.

After the opposed ends 160.1, 160.2 of the suture elements 160 on the suture holder parts 116.1, 116.1 have been paired in this fashion, the opposed ends of each suture element can be disengaged from the needles 117 and tied together to form sutures joining the target vessel 182 and the donor vessel 196 together adjacent their apertures thereby to form a side-to-side anastomosis between them. Tying of the suture elements can be performed manually. Instead, appropriate suture tying devices can be used. Advantageously, use can be made of an appropriate suture-handling device to render the task of tying the opposed portions of the suture elements together more manageable. An example of such a suture-handling device is disclosed in Applicant's co-pending patent application No. 09/610,099, filed on Jun. 6, 2000, entitled "Suture Comb" the full disclosure of which is herein incorporated by reference.

Such a suture-handling device is indicated by reference numeral 210 in FIGS. 16 and 17. As indicated, the device 210 has five slots 210.1, 210.2, 210.3, 210.4 and 210.5. The slots 210.1, 210.2, 210.3, 210.4, 210.5 diverge outwardly relative to one another in a direction away from a leading end 212 of the device 210. Each slot 210.1, 210.2, 210.3, 210.4, 210.5 has a mouth 210.1A, 210.2A, 210.3A, 210.4A, 210.5A at the end 212. The mouths are laterally spaced apart relative to one another by a distance corresponding to spacings between the paired up ends of the suture elements 160. As can best be seen with reference to FIG. 16, since the spacing between the mouths 210.1A, 210.2A, 210.3A, 210.4A, 210.5A corresponds with the spacing between the paired up ends of the suture elements on the parts 116.1, 116.1, the suture-handling device 210 can readily be passed laterally across paired portions of the suture elements 160 adjacent their ends, as indicated by arrow J. As the suture-handling device 210 is passed laterally across the paired portions of the suture elements 160 in this fashion, the paired end portions of the suture elements enter the mouths 210.1A, 210.2A, 210.3A, 210.4A, 210.5A and ride along the slots 210.1, 210.2, 210.3, 210.4, 210.5. As the paired end portions ride along the diverging portions of the slots 210.1, 210.2, 210.3, 210.4, 210.5 of the device 210, the paired portions become spaced laterally further apart relative to one another, as indicated by the arrows I in FIG. 17 of the drawings. By increasing the lateral spacing between the paired end portions of the suture elements 160 in this fashion, manual pick up of the opposed end portions of the individual suture elements is made easier and more manageable. Advantageously, the device 210 is arranged to retain the paired end portions thereon after the lateral spacing between the paired up end portions has been increased. In this way, the paired up end portions can be held in paired relationships so that each set of paired up end portions can be picked up from the device 210 separately of the others and tied together, while the end portions of the other suture elements are retained in paired relationships on the device 210.

It will be appreciated that the parts 116.2, 116.2 can be paired up in a similar fashion to that described above with reference to the parts 116.1, 116.1. Thereafter, another device, similar to the device 210, can be used to hold the paired up end portions of the other suture elements together, so that they too can be picked up separately and tied, while the paired up end portions of the other suture elements are held in paired up relationships on the other device 210.

Referring to FIG. 18, the target vessel 182 and the donor vessel 196 are shown in a position adjacent each other and ready for the opposed ends 160.1, 160.2 of the suture elements 160 to be tied together, thereby to form sutures extending between the walls of the vessels 182, 196. The vessels can be brought into a position adjacent each other manually, while pulling opposed portions of the suture elements 160. In this way the vessels can be caused to ride along the suture elements 160 until they are positioned as schematically shown in FIG. 18. Thereafter, the opposed ends of the suture elements can be tied together to form sutures joining the vessels together so as to form the side-to-side anastomosis between them. After the sutures have been tied, or secured, a side-to-side anastomosis similar to the side-to-side anastomosis shown in FIG. 1C is formed between the vessels 182, 196.

A needle deployment system, in accordance with the invention, which is incorporated in another suture placement system, which can be used advantageously to form an end-to-side anastomosis, as indicated in FIG. 1B of the drawings, will now be described with reference to FIGS. 19 to 28. In FIGS. 19 to 28 like reference numerals have been used to designate similar parts and features unless otherwise stated. Furthermore, the system 310 is used in a fashion similar to that of the system 110, unless otherwise stated.

As can best be seen with reference to FIG. 19 of the drawings, the suture placement system, which is generally indicated by reference numeral 310, is similar to the system 110, save that instead of the device 114, the system 310 has a different suture placement device incorporating a needle deployment device in accordance with the invention. The different suture placement device is indicated generally by reference numeral 312 and is arranged for placing sutures through a vessel wall adjacent a mouth of a vessel, as will be described in greater detail herein below.

Referring to FIG. 20 of the drawings, the suture placement device 312 comprises a body 314 and two suture holder retainers 316, 318. Each retainer 316, 318 is mounted on the body 314 by means of a pivotal connection 320, 322 respectively. The device 312 further comprises a vessel support shaft 324 for receiving an end portion of a vessel, or graft, or the like, thereon. The shaft 324 is mounted on the body 314. The shaft 324 is arranged to be passed through the mouth of the vessel so that the vessel can be supported at an operative position on the shaft 324 at which position the device 312 can pass a plurality of suture elements through the wall of the vessel adjacent its mouth.

The body 314 comprises a piston and cylinder arrangement similar to that of the devices 112, 114 described above. The piston and cylinder arrangement is indicated schematically and generally by reference numeral 326. A socket for receiving an end of the conduit portion 121.2 of the flexible elongate member 120 is indicated at 327. When the conduit portion 121.2 is connected to the socket 327, a chamber within the body 314 is connected in fluid flow communication with a female Luer-type connector in a fashion similar to that of the device 114 in the system 110.

Referring now to FIGS. 21 to 23 of the drawings, the shaft 324 defines a plurality of longitudinally extending passages indicated schematically by reference numeral 328. The passages 328 have bends 330 leading to mouths 332 opening at an outer surface 334 of the shaft 324. As can best be seen with reference to FIGS. 22 and 23, a needle 335 is received in each of the passages 328. Each needle 335 defines a pointed end 335.1. An actuation member in the form of an elongate pin or rod formation 336 is received in each of the passages 328 immediately behind the needles 335. The pin formations 336 are operatively associated with the piston on the body 314 so that the formations 336 are caused to advance, as indicated by arrow K, in response to the piston being caused to advance within its associated cylinder. It will be appreciated that the piston of the device 312 is caused to advance within its associated cylinder in a manner similar to that of the piston and cylinder arrangement of the devices 112, 114 as described above, namely, by depressing a plunger of a syringe connected in fluid flow communication with the female Luer-type connector 140, as can best be seen with reference to FIG. 19.

With reference to FIG. 23, upon advancement of the pin formations 336 along the passages 328, the needles 335 are caused to advance along the passages 328 also. The needles 335 are caused to advance such that their pointed ends 335.1 are pushed out of the mouths 332 and laterally outwardly from the surface 334 of the shaft 324.

Referring now to FIG. 24 of the drawings, ends 338.1 of a plurality of suture elements 338 are operatively engaged to end portions of the needles 335 adjacent the ends 335.1 of the needles 335. The ends 338.1 of the suture elements 338 can be operatively engaged to the end portions of the needles 335 in any appropriate manner. For example, the end portions of the needles 335 can have laterally extending apertures through which end portions of the suture elements 338 can be threaded. The suture elements 338 typically extend along the outer surface 334 of the shaft 324, along an outer surface of the body 314 and into the suture container portion 120.3 of the elongate flexible member 120, as can best be seen with reference to FIG. 19 of the drawings, in a fashion similar to that described above with reference to the system 110. It will be appreciated that opposed ends of the suture elements 338 are held on the suture support 118 of the device 112 of the system 310 in a fashion similar to that of the ends 160.1 of the suture elements 160 of the system 110.

The operation of the device 312 will now be described with reference to FIGS. 25 to 27 of the drawings. It will be appreciated that opposed ends of the suture elements 338 are placed through a vessel wall by means of the device 112 and adjacent an incision in that vessel wall in a manner similar to that described above with reference to the system 110.

Referring to FIG. 25, an end portion 350.1 of a vessel, or graft, indicated generally by reference numeral 350, is shown in a received condition on the shaft 324. The end portion 350.1 of the vessel 350 was positioned on the shaft 324 by displacing the suture holder arrangements 316, 318 angularly about the pivotal connections 320, 322 into open positions and then passing the end portion 350.1 of the vessel 350 over the shaft 324. Conveniently, marks 352 are provided on the shaft 324 to indicate an appropriate position of an end 350.3 of the vessel 350 on the shaft 334 so as to enable the suture elements to be passed through a vessel wall 350.2 of the vessel 350 at an appropriate distance from the end 350.3. In FIG. 25, only the suture holder retainer 318 is shown in an open condition. Typically, both retainers 316, 318 are opened so as to pass the vessel portion 350.1 over the shaft 324. When the end portion 350.1 of the vessel 350 has been positioned such that its end 350.3 is in register with the marks 352 on the shaft 324, the retainers 316, 318 are displaced angularly about the pivotal connections 320, 322 into a closed condition in which the end portion 350.1 of the vessel 350 is embraced between the retainers 316, 318 and the shaft 324. FIG. 25 shows the retainer 316 having been displaced from an open condition into a closed condition after the portion 350.1 of the vessel 350 has been appropriately positioned on the shaft 324.

Conveniently, the vessel 350 is shaped to have an angled, or inclined, end 350.3 so as to permit an end-to-side anastomosis to be formed in which the one vessel extends from the other at an acute angle, as can best be seen with reference to FIG. 1B of the drawings. The marks 352 are formed on the shaft 324 to extend circumferentially around the shaft 324 so as to align with a vessel having such an inclined end 350.3.

FIG. 26 shows the portion 350.1 of the vessel 350 having been received on the shaft 324 and further shows both retainers 316, 318 in closed conditions. As can best be seen with reference to FIG. 25 of the drawings, the retainers 316, 318 are provided with cooperating engaging formations so as to lockingly engage with each other when in their closed conditions. Conveniently, the engaging formations comprise tongue members 354, 354 and slot arrangements 356, 356 for snap-lockingly receiving the tongue members 354, 354. After the end portion 350.1 of the vessel 350 has been received on the shaft 324 and the retainers 316, 318 have been closed so as to engage lockingly with each other, the needles 335 bearing the ends 338.1 of the suture elements 338 are caused to advance along the passages 328. This is achieved by means of the pin formations 336 being displaced along the passages 328 in response to actuating a syringe connected in fluid flow communication with the female Luer-type connector 140 operatively associated with the device 312. As the needles 335 are caused to advance in this fashion, the ends 335.1 of the needles 335 are driven through the wall 350.2 of the vessel 350 adjacent its mouth. The ends 338.1 of the suture elements 338 are passed through the vessel wall 350.2 together with the ends 335.1 of the needles 335, since the ends 338.1 of the suture elements 338 are appropriately attached to the ends of the needles. After the ends 335.1 of the needles 335 have passed through the vessel wall 350.2, the ends 335.1 are driven into suture holders 358, 360 releasably mounted on the suture holder arrangements 316, 318 to be held captive by the holders 358, 360. The retainers 316, 318 are then angularly displaced about the pivotal connections 320, 322 into their open conditions to enable the vessel 350 to be removed from the shaft 324. The suture holders 358, 360 are removed from the retainers 316, 318, while the needle ends 335.1, and consequently also the ends 338.1 of the suture elements 338, are held captive on the suture holders 358, 360. To remove the holders 358, 360 from the retainers 316, 318, hand grippable portions 358.1, 360.1 of the holders 358, 360 are typically manipulated to cause the holders 358, 360 to be slid along slots 362 defined by the retainers 316, 318. As can best be seen in FIG. 24 of the drawings, each retainer 316, 318 has a part annular shoulder formation 364 arranged to retain the holders 358, 360 in a mounted condition on the retainers 316, 318. When the holders 358, 360 are removed from their associated retainers 316, 318, the hand grippable portions 358.1, 360.1 are manipulated resiliently to urge the holders over the annular shoulder formations 364. FIG. 28 shows the end portion 350.1 of the vessel 350 having been removed from the shaft 324 and further shows the holders 358, 360 having been removed from the associated retainers 316, 318.

Referring now to FIGS. 28A and 28B of the drawings, the suture holder 358 is shown in greater detail, and after it has been removed from its associated retainer 316. In FIGS. 28A and 28B, the holder 358 is shown after the needles 335 have been passed through the portion of the vessel 350 and into engagement with the holder 358. In FIG. 28A, the suture holder is shown having a shape corresponding to the shape which it has when mounted on its associated retainer 316. When mounted on the retainer 316, opposed flange portions 358.2 of the suture holder 358 are held in a resiliently deformed condition such that an inner surface 358.3 defined by the flange portions 358.2 extends generally along a circular circumference so as to extend snugly around the vessel portion 350.1 when held between the retainers 316, 318 and the shaft 324. The suture holder 358 is typically made from a resilient material, such as silicone, or the like. In FIG. 28B, the suture holder 358 is shown after having been removed from its associated retainer 316. After having been removed, the flange portions 358.2 take up a relaxed condition in which they have a straighter profile than in the case when mounted on the retainer 316. In this relaxed condition, the spacing between the needle ends 335.1 on which the ends 338.1 of the suture elements 338 are carried is greater than in the case when the holder 358 was mounted on the retainer 316. The holder 358 is designed so that when in its relaxed condition, the spacing between adjacent suture element ends 338.1 on the needles 335 generally corresponds with the spacing between adjacent suture element ends when held on the parts 116.1, 116.2 of the suture holder of the device 112.

To form the end-to-side anastomosis, the device 112 is used to place the opposed ends of the suture elements 338 through another vessel wall adjacent an incision in the other vessel wall in a fashion similar to that described above with reference to the system 110.

After the suture elements 338 have been placed through the wall of the portion 350.1 of the vessel 350 adjacent its mouth, as described above, and after opposed ends of the suture elements 338 have been placed through a vessel wall adjacent an incision in the vessel wall by the device 112, in a manner similar to that described above, the suture holders 358, 360 are paired up with the suture holders 116.1, 116.2 of the device 112. Accordingly, in this fashion, opposed ends of the same suture elements are paired up with each other. The paired up end portions of the suture elements can then be passed into the slots of a suture handling device as described above, for example. After having been received in the slots of the suture handling device as described above, the suture elements can be removed from the suture handling device and can be tied, or otherwise secured together, so as to form sutures between the vessels thereby to form an end-to-side anastomosis between the vessels.

Although certain embodiments of the invention have been described above in detail for purposes of clarity and understanding, it will be appreciated that the invention has been described with reference to the above embodiments by way of example only, and that modifications or changes can be made without detracting from the essence of the invention. For example, although reference is made to needles in the above embodiments, it is to be appreciated that this term is to be interpreted broadly to include elongate members not necessarily having pointed ends. The ends of the needles may be blunt or may have other formations, such as hook-like formations, or the like, which can be arranged to engage ends of suture elements, or the like. Accordingly, the scope of the invention is defined by the appended claims with due regard to equivalents of the claimed elements or features.

What is claimed is:

1. A needle deployment device comprising:
a body;
a plurality of medical needles displaceably mounted on the body;
an actuator on the body, the actuator being actuatable in response to pressurizing a fluid so as to cause the needles to displace relative to the body;
a suture support on the body; and
a plurality of suture elements, each suture element having an end, the end of each suture element releasably held on the suture support, such that when the needles are advanced relative to the body, the needles engage the ends of the suture elements.

2. The needle deployment device of claim 1, wherein the actuator comprises a piston displaceably mounted in a cylinder, the piston being displaceable relative to the cylinder in response to pressurizing the fluid.

3. The needle deployment device of claim 2, wherein the needles are operatively connected to the piston so that the needles displace relative to the body in response to the piston displacing relative to the cylinder.

4. The needle deployment device of claim 3, wherein a chamber is defined in the cylinder on one side of the piston, the chamber being operatively connectable to a fluid source to be in fluid flow communication with the fluid source such that the piston can be caused to displace relative to the cylinder in response to pressurizing fluid in the chamber by passing fluid into the chamber from the fluid source.

5. The needle deployment device of claim 4, which further comprises a conduit operatively connected to the chamber, the conduit being connectable to the fluid source.

6. The needle deployment device of claim 5, wherein the conduit is in the form of a flexible length of tubing.

7. The needle deployment device of claim 6, wherein the length of tubing is formed of a plastics material.

8. The needle deployment device of claim 5, wherein the conduit is arranged to be connected to a fluid source contained in a syringe.

9. The needle deployment device of claim 8, which comprises a connector on the conduit for connection to the syringe.

10. The needle deployment device of claim 9, wherein the connector is a Luer type connector for connection with a complementary Luer type connector on the syringe.

11. The needle deployment device of claim 10, which comprises a relief valve for relieving fluid pressure in the chamber should the pressure in the chamber exceed a predetermined amount.

12. The needle deployment device of claim 11, wherein the relief valve is operatively connected with the conduit.

13. A medical system comprising:
at least two bodies;
a plurality of needles displaceably mounted on each body;
an actuator on each body, each actuator being selectively actuatable in response to pressurizing a fluid so as to cause the needles to be displaced relative to their associated bodies; and
a plurality of suture elements extending between the bodies such that an end of each suture element is supported on one of the bodies and opposed ends of the suture elements are supported on the other of the bodies.

14. The medical system of claim 13, wherein each actuator comprises a piston displaceably mounted in a cylinder, each piston being displaceable relative to its associated cylinder in response to pressurizing fluid.

15. The medical system of claim 14, wherein the needles are operatively connected to the pistons so that the needles are displaceable relative to the bodies in response to the pistons displacing relative to the cylinders.

16. The medical system of claim 15, wherein a chamber is defined in each cylinder on one side of its associated piston, the chambers being operatively connectable with fluid sources to be in fluid flow communication with the fluid sources such that the pistons can be caused selectively to displace relative to the cylinders in response to pressurizing fluid at the fluid sources.

17. The medical system of claim 16, which comprises a conduit connected in fluid flow communication with each cylinder, each conduit being connectable to a fluid source.

18. The medical system of claim 17, wherein the conduits are in the form of flexible lengths of tubing.

19. The medical system of claim 18, wherein the lengths of tubing are formed of a plastics material.

20. The medical system of claim 17, wherein each conduit is arranged to be connected to a source of fluid contained in a syringe.

21. The medical system of claim 20, which comprises a connector on each conduit for connection to a syringe.

22. The medical system of claim 21, wherein each connector is a Luer type connector for connection with a complementary Luer type connector on a syringe.

23. The medical system of claim 22, which comprises a relief valve operatively associated with each chamber so as to relieve pressure in the chambers should the pressure in the chambers exceed predetermined amounts.

24. The medical system of claim 23, wherein the relief valves are operatively connected with the conduits.

25. The medical system of claim 24, wherein the needles on each body are arranged to place a suture at a surgical site on a patient body.

26. The medical system of claim 13, which comprises a suture element container extending between the bodies, the suture element container being arranged to contain central portions of the suture elements such that the suture elements can be drawn from the container.

27. The medical system of claim 26, in which the container comprises a length of tubing defining a longitudinally extending slit for enabling the suture elements to be drawn from the container through the slit.

28. The medical system of claim 27, wherein the bodies are connected one to another by means of a flexible elongate member, the elongate member defining two opposed longitudinally extending lumen formations, the one lumen formation defining the suture element container and the other conduit formation defining a portion of the conduit extending from at least one of the chambers of the bodies to its associated connector.

29. The medical system of claim 28, which further comprises a second elongate member which comprises longitudinally extending lumen formations, an end of the second elongate member being connected to the first elongate member such that each of the conduits extending from the chambers of the bodies is defined in part by a portion of the conduit formation on the first elongate member and one of the conduit formations defined by the second elongate member.

30. The medical system of claim 29, which comprises a pivotal connection connecting the second elongate member to the first elongate member.

31. A method of performing a medical procedure, the method comprising:
   positioning a needle deployment device adjacent tissue of a patient body;
   pressurizing a fluid;
   actuating an actuator of the needle deployment device in response to pressurizing the fluid;
   causing a plurality of needles to displace in response to actuating the actuator;
   causing free ends of the needles to pass through the tissue in response to causing the needles to displace; and
   causing the free ends of the needles operatively to engage with ends of suture elements.

32. The method of claim 31, wherein the needle deployment device comprises a body and the actuator comprises a piston and cylinder arrangement on the body, actuating the actuator comprising causing the piston to displace relative to the cylinder in response to pressurizing the fluid.

33. The method of claim 32, wherein the plurality of needles are displaceably mounted on the body, causing the plurality of needles to displace in response to actuating the actuator comprising causing the needles to displace relative to the body.

34. The method of claim 33, wherein the needles are operatively connected with the piston of the actuator, causing the needles to displace relative to the body comprising causing the needles to displace in sympathy with the piston displacing relative to the cylinder.

35. The method of claim 34, wherein the cylinder of the piston and cylinder arrangement defines a chamber on one side of the piston, pressurizing the fluid comprising passing a fluid into the chamber to cause the piston to displace relative to the cylinder.

36. The method of claim 35, wherein the chamber is operatively connected to a source of fluid, passing fluid into the chamber comprising pressurizing the fluid at the source to cause fluid to pass into the chamber.

37. The method of claim 36, wherein the source of fluid is in a syringe, pressurizing the fluid at the source comprising causing a piston of the syringe to displace in a chamber of the syringe.

38. The method of claim 31, which further comprises causing the needles to displace in an opposed direction after having operatively engaged the ends of the suture elements to draw the suture elements through the tissue.

* * * * *